(12) United States Patent
Kwon et al.

(10) Patent No.: US 10,982,244 B2
(45) Date of Patent: Apr. 20, 2021

(54) MODIFIED HOMOSERINE DEHYDROGENASE AND METHOD FOR PRODUCING HOMOSERINE OR L-AMINO ACID DERIVED FROM HOMOSERINE USING THE SAME

(71) Applicant: CJ CHEILJEDANG CORPORATION, Seoul (KR)

(72) Inventors: Su Yon Kwon, Suwon-si (KR); Kwang Woo Lee, Suwon-si (KR); Lan Huh, Suwon-si (KR); Kyungrim Kim, Seoul (KR); Mina Baek, Yongin-si (KR); Seung-ju Son, Anyang-si (KR); Jaemin Lee, Jijeongbu-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/478,286

(22) PCT Filed: Apr. 10, 2019

(86) PCT No.: PCT/KR2019/004250
§ 371 (c)(1),
(2) Date: Jul. 16, 2019

(87) PCT Pub. No.: WO2020/130236
PCT Pub. Date: Jun. 25, 2020

(65) Prior Publication Data
US 2020/0340022 A1  Oct. 29, 2020

(30) Foreign Application Priority Data

Dec. 21, 2018 (KR) .................. 10-2018-0167599

(51) Int. Cl.
| | |
|---|---|
| *C12N 1/21* | (2006.01) |
| *C12N 9/04* | (2006.01) |
| *C12P 13/12* | (2006.01) |
| *C12P 13/06* | (2006.01) |
| *C12P 13/08* | (2006.01) |

(52) U.S. Cl.
CPC ............ *C12P 13/06* (2013.01); *C12N 9/0006* (2013.01); *C12P 13/08* (2013.01); *C12P 13/12* (2013.01); *C12Y 101/01003* (2013.01)

(58) Field of Classification Search
None
See application file for complete search history.

(56) References Cited

U.S. PATENT DOCUMENTS

| | | | |
|---|---|---|---|
| 5,124,257 A | 6/1992 | Azizian et al. | |
| 6,649,379 B1 | 11/2003 | Archer et al. | |
| 7,332,310 B2 | 2/2008 | Nakagawa et al. | |
| 8,283,152 B2 | 10/2012 | Kim et al. | |
| 8,609,396 B2 | 12/2013 | Kim et al. | |
| 9,127,257 B2 | 9/2015 | Kim et al. | |
| 2009/0298136 A1* | 12/2009 | Zelder | C12P 13/12 435/113 |

FOREIGN PATENT DOCUMENTS

| | | |
|---|---|---|
| CN | 101208427 A | 6/2008 |
| KR | 10-0057684 B1 | 8/1992 |
| KR | 10-0159812 B1 | 11/1998 |
| KR | 10-0620092 B1 | 9/2006 |
| KR | 10-2008-0028940 A | 4/2008 |
| KR | 10-0924065 B1 | 10/2009 |
| KR | 10-1167853 B1 | 7/2012 |
| KR | 10-1429815 B1 | 8/2014 |
| KR | 10-2000-0041583 A | 7/2015 |
| KR | 10-1632642 B1 | 6/2016 |
| KR | 10-1783170 B1 | 9/2017 |
| WO | 2004/108894 A2 | 12/2004 |
| WO | 2007/086618 A1 | 8/2007 |
| WO | 2009/051262 A1 | 4/2009 |
| WO | 2010/084995 A2 | 7/2010 |

OTHER PUBLICATIONS

Morbach et al., Engineering the homoserine dehydrogenase and threonine dehydratase control points to analyse flux towards L-isoleucine in Corynebacterium glutamicum, Appl. Microbiol. Biotechnol. 45, 1996, 612-20. (Year: 1996).*
Reinscheid et al., Analysis of a Corynebacterium glutamicum hom Gene Coding for a Feedback-Resistant Homoserine Dehydrogenase, J. Bacteriol. 173, 1991, 3228-30. (Year: 1991).*
Archer et al., "A C-terminal deletion in *Corynebacterium glutamicum* homoserine dehydrogenase abolishes allosteric inhibition by L -threonine," *Gene* 107:53-59, 1991.
Eikmanns et al., "Amplification of three threonine biosynthesis genes in *Corynebacterium glutamicum* and its influence on carbon flux in different strains," *Applied Microbiology and Biotechnology* 34:617-622, 1991.
"Homoserine dehydrogenase," UniProtKB, https://www.uniprot.org/uniprot/P08499, accessed: Jul. 8, 2019.
Morbach et al., "Engineering the homoserine dehydrogenase and threonine dehydratase control points to analyse flux towards L -isoleucine in *Corynebacterium glutamicum*," *Appl Microbiol Biotechnol* 45:612-620, 1996.
Morbach et al., " L -Isoleucine Production with *Corynebacterium glutamicum*: Further Flux Increase and Limitation of Export," *Applied and Environmental Microbiology* 62(12):4345-4351, 1996.

(Continued)

*Primary Examiner* — Robert B Mondesi
*Assistant Examiner* — Todd M Epstein
(74) *Attorney, Agent, or Firm* — Seed IP Law Group LLP

(57) ABSTRACT

The present disclosure relates to modified homoserine dehydrogenase and a method for producing homoserine or a homoserine-derived L-amino acid using the same.

20 Claims, No Drawings
Specification includes a Sequence Listing.

(56) References Cited

OTHER PUBLICATIONS

Peoples et al., "Nucleotide sequence and fine structural analysis of the *Corynebacterium glutamicum hom-thrB* operon," *Molecular Microbiology* 2(1):63-72, 1988. (11 pages).
Rey et al., "The putative transcriptional repressor McbR, member of the TetR-family, is involved in the regulation of the metabolic network directing the synthesis of sulfur containing amino acids in *Corynebacterium glutamicum*," *Journal of Biotechnology* 103:51-65, 2003.
Takeda et al., "Detection of K-ras Mutation in Sputum by Mutant-Allele-Specific Amplification (MASA)," *Human Mutation* 2:112-117, 1993.
Van der Rest et al., "A heat shock following electroporation induces highly efficient transformation of *Corynebacterium glutamicum* with xenogeneic plasmid DNA," *Applied Microbiology and Biotechnology* 52:541-545, 1999.
PCT/KR2019/00006083, Modified Homoserine Dehydrogenase and method for Producing Homoserine or L-Amino Acid Derived from Homoserine Using the Same.

\* cited by examiner

SEQUENCE LISTING

```
<160> NUMBER OF SEQ ID NOS: 41

<210> SEQ ID NO 1
<211> LENGTH: 445
<212> TYPE: PRT
<213> ORGANISM: Artificial Sequence
<220> FEATURE:
<223> OTHER INFORMATION: homoserine dehydrogenase

<400> SEQUENCE: 1

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
                20                  25                  30

Val Met Arg Leu Met Thr Glu Tyr Gly Asp Glu Leu Ala His Arg Ile
            35                  40                  45

Gly Gly Pro Leu Glu Val Arg Gly Ile Ala Val Ser Asp Ile Ser Lys
        50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
                85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
        115                 120                 125

Leu Ala Asp Ala Ala Glu Ala Ala Asn Val Asp Leu Tyr Phe Glu Ala
    130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
        195                 200                 205

Ala Asp Val Glu Gly His Asp Ala Ala Ser Lys Ala Ala Ile Leu Ala
    210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
        275                 280                 285

Val Ser His Pro Leu Ala Ser Val Asn Lys Ser Phe Asn Ala Ile Phe
    290                 295                 300
```

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
            325                 330                 335

Ala Arg Asn Lys Val His Gly Arg Ala Pro Gly Glu Ser Thr Tyr
        340                 345                 350

Ala Asn Leu Pro Ile Ala Asp Phe Gly Glu Thr Thr Arg Tyr His
    355                 360                 365

Leu Asp Met Asp Val Glu Asp Arg Val Gly Val Leu Ala Glu Leu Ala
370                 375                 380

Ser Leu Phe Ser Glu Gln Gly Ile Ser Leu Arg Thr Ile Arg Gln Glu
385                 390                 395                 400

Glu Arg Asp Asp Asp Ala Arg Leu Ile Val Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
        435                 440                 445

<210> SEQ ID NO 2
<211> LENGTH: 1338
<212> TYPE: DNA
<213> ORGANISM: Artificial Sequence
<220> FEATURE:
<223> OTHER INFORMATION: hom gene

<400> SEQUENCE: 2
atgacctcag catctgcccc aagctttaac cccggcaagg gtcccggctc agcagtcgga      60
attgcccttt taggattcgg aacagtcggc actgaggtga tgcgtctgat gaccgagtac     120
ggtgatgaac ttgcgcaccg cattggtggc ccactggagg ttcgtggcat tgctgtttct     180
gatatctcaa agccacgtga aggcgttgca cctgagctgc tcactgagga cgcttttgca     240
ctcatcgagc gcgaggatgt tgacatcgtc gttgaggtta cggcggcat tgagtaccca     300 cgtgaggtag ttctcgcagc tctgaaggcc ggcaagtctg ttgttaccgc caataaggct     360
cttgttgcag ctcactctgc tgagcttgct gatgcagcgg aagccgcaaa cgttgacctg     420
tacttcgagg ctgctgttgc aggcgcaatt ccagtggttg ccccactgcg tcgctccctg     480
gctggcgatc agatccagtc tgtgatgggc atcgttaacg gcaccaccaa cttcatcttg     540
gacgccatgg attccaccgg cgctgactat gcagattctt tggctgaggc aactcgtttg     600
ggttacgccg aagctgatcc aactgcagac gtcgaaggcc atgacgccgc atccaaggct     660
gcaattttgg catccatcgc tttccacacc cgtgttaccg cggatgatgt gtactgcgaa     720
ggtatcagca acatcagcgc tgccgacatt gaggcagcac agcaggcagg ccacaccatc     780
aagttgttgg ccatctgtga aagttcacc aacaaggaag aaagtcggc tatttctgct     840 cgcgtgcacc cgactctatt acctgtgtcc cacccactgg cgtcggtaaa caagtccttt     900
aatgcaatct tgttgaagc agaagcagct ggtcgcctga tgttctacgg aaacggtgca     960
ggtggcgcgc caaccgcgtc tgctgtgctt ggcgacgtcg ttggtgccgc acgaaacaag    1020
gtgcacggtg gccgtgctcc aggtgagtcc acctacgcta acctgccgat cgctgatttc    1080
ggtgagacca ccactcgtta ccacctcgac atggatgtgg aagatcgcgt gggggttttg    1140
gctgaattgg ctagcctgtt ctctgagcaa ggaatctccc tgcgtacaat ccgacaggaa    1200
gagcgcgatg atgatgcacg tctgatcgtg gtcacccact ctgcgctgga atctgatctt    1260

```
tcccgcaccg ttgaactgct gaaggctaag cctgttgtta aggcaatcaa cagtgtgatc    1320
cgcctcgaaa gggactaa                                                  1338

<210> SEQ ID NO 3
<211> LENGTH: 930
<212> TYPE: DNA
<213> ORGANISM: Artificial Sequence
<220> FEATURE:
<223> OTHER INFORMATION: thrB gene

<400> SEQUENCE: 3
atggcaattg aactgaacgt cggtcgtaag gttaccgtca cggtacctgg atcttctgca      60
aacctcggac ctggctttga cactttaggt ttggcactgt cggtatacga cactgtcgaa     120
gtggaaatta ttccatctgg cttggaagtg aagttttttg gcgaaggcca aggcgaagtc     180
cctcttgatg gctcccacct ggtggttaaa gctattcgtg ctggcctgaa ggcagctgac     240
gctgaagttc ctggattgcg agtggtgtgc cacaacaaca ttccgcagtc tcgtggtctt     300
ggctcctctg ctgcagcggc ggttgctggt gttgctgcag ctaatggttt ggcggatttc     360
ccgctgactc aagagcagat tgttcagttg tcctctgcct ttgaaggcca cccagataat     420
gctgcggctt ctgtgctggg tggagcagtg gtgtcgtgga caaatctgtc tatcgacggc     480
aagagccagc cacagtatgc tgctgtacca cttgaggtgc aggacaatat tcgtgcgact     540
gcgctggttc ctaatttcca cgcatccacc gaagctgtgc gccgagtcct tcccactgaa     600
gtcactcaca tcgatgcgcg atttaacgtg tcccgcgttg cagtgatgat cgttgcgttg     660
cagcagcgtc ctgatttgct gtgggagggt actcgtgacc gtctgcacca gccttatcgt     720
gcagaagtgt tgcctattac ctctgagtgg gtaaaccgcc tgcgcaaccg tggctacgcg     780 gcatacctttt ccggtgccgg cccaaccgcc atggtgctgt ccactgagcc aattccagac     840
aaggttttgg aagatgctcg tgagtctggc attaaggtgc ttgagcttga ggttgcggga     900
ccagtcaagg ttgaagttaa ccaaccttag                                     930

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
ctgcgacagc atggaact                                                   18

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
caacgacaaa cgcccatc                                                   18

<210> SEQ ID NO 6
<211> LENGTH: 2778
<212> TYPE: DNA
<213> ORGANISM: Artificial Sequence
<220> FEATURE:
<223> OTHER INFORMATION: gene fragment
```

```
<400> SEQUENCE: 6
ctgcgacagc atggaactca gtgcaatggc tgtaaggcct gcaccaacaa tgattgagcg      60
aagctccaaa atgtcctccc cgggttgata ttagatttca taaatatact aaaaatcttg     120
agagttttc  cgttgaaaac taaaaagctg gaaggtgaa  tcgaatttcg ggctttaaa      180
gcaaaaatga acagcttggt ctatagtggc taggtaccct ttttgttttg gacacatgta     240
gggtggccga acaaagtaa  taggacaaca acgctcgacc gcgattattt ttggagaatc     300
atgacctcag catctgcccc aagctttaac cccggcaagg gtcccggctc agcagtcgga     360
attgcccttt taggattcgg aacagtcggc actgaggtga tgcgtctgat gaccgagtac     420
ggtgatgaac ttgcgcaccg cattggtggc ccactggagg ttcgtggcat tgctgtttct     480
gatatctcaa agccacgtga aggcgttgca cctgagctgc tcactgagga cgcttttgca     540
ctcatcgagc gcgaggatgt tgacatcgtc gttgaggtta tcggcggcat tgagtaccca     600
cgtgaggtag ttctcgcagc tctgaaggcc ggcaagtctg ttgttaccgc caataaggct     660
cttgttgcag ctcactctgc tgagcttgct gatgcagcgg aagccgcaaa cgttgacctg     720
tacttcgagg ctgctgttgc aggcgcaatt ccagtggttg gcccactgcg tcgctccctg     780
gctggcgatc agatccagtc tgtgatgggc atcgttaacg gcaccaccaa cttcatcttg     840
gacgccatgg attccaccgg cgctgactat gcagattctt ggctgaggc  aactcgtttg     900
ggttacgccg aagctgatcc aactgcagac gtcgaaggcc atgacgccgc atccaaggct     960
gcaattttgg catccatcgc tttccacacc cgtgttaccg cggatgatgt gtactgcgaa    1020
ggtatcagca acatcagcgc tgccgacatt gaggcagcac agcaggcagg ccacaccatc    1080
aagttgttgg ccatctgtga agttcacc   aacaaggaag gaaagtcggc tatttctgct    1140
cgcgtgcacc cgactctatt acctgtgtcc cacccactgg cgtcggtaaa caagtccttt    1200
aatgcaatct tgttgaagc  agaagcagct ggtcgcctga tgttctacgg aaacggtgca    1260
ggtggcgcgc caaccgcgtc tgctgtgctt ggcgacgtct tggtgccgc  acgaaacaag    1320
gtgcacggtg gccgtgctcc aggtgagtcc acctacgcta acctgccgat cgctgatttc    1380
ggtgagacca ccactcgtta ccacctcgac atggatgtgg aagatcgcgt gggggttttg    1440
gctgaattgg ctagcctgtt ctctgagcaa ggaatctccc tgcgtacaat ccgacaggaa    1500
gagcgcgatg atgatgcacg tctgatcgtg gtcaccccact ctgcgctgga atctgatctt   1560
tcccgcaccg ttgaactgct gaaggctaag cctgttgtta aggcaatcaa cagtgtgatc    1620
cgcctcgaaa gggactaatt ttactgacat ggcaattgaa ctgaacgtcg gtcgtaaggt    1680
taccgtcacg gtacctggat cttctgcaaa cctcggacct ggctttgaca ctttaggttt    1740
ggcactgtcg gtatacgaca ctgtcgaagt ggaaattatt ccatctggct tggaagtgga    1800
agttttggc  gaaggccaag gcgaagtccc tcttgatggc tcccacctgg tggttaaagc    1860
tattcgtgct ggcctgaagg cagctgacgc tgaagttcct ggattgcgag tggtgtgcca    1920
caacaacatt ccgcagtctc gtggtcttgg ctcctctgct gcagcggcgg ttgctggtgt    1980
tgctgcagct aatggtttgg cggatttccc gctgactcaa gagcagattg ttcagttgtc    2040
ctctgccttt gaaggccacc agataatgc  tgcggcttct gtgctgggtg gagcagtggt    2100
gtcgtggaca aatctgtcta tcgacggcaa gagccagcca cagtatgctg ctgtaccact    2160
tgaggtgcag gacaatattc gtgcgactgc gctggttcct aatttccacg catccaccga    2220
agctgtgcgc cgagtccttc ccactgaagt cactcacatc gatgcgcgat taacgtgtc     2280
ccgcgttgca gtgatgatcg ttgcgttgca gcagcgtcct gatttgctgt gggagggtac    2340
```

| | |
|---|---|
| tcgtgaccgt ctgcaccagc cttatcgtgc agaagtgttg cctattacct ctgagtgggt | 2400 |
| aaaccgcctg cgcaaccgtg gctacgcggc ataccttttcc ggtgccggcc caaccgccat | 2460 |
| ggtgctgtcc actgagccaa ttccagacaa ggttttggaa gatgctcgtg agtctggcat | 2520 |
| taaggtgctt gagcttgagg ttgcgggacc agtcaaggtt gaagttaacc aaccttaggc | 2580 |
| ccaacaagga aggccccctt cgaatcaaga aggggggcctt attagtgcag caattattcg | 2640 |
| ctgaacacgt gaaccttaca ggtgcccggc gcgttgagtg gtttgagttc cagctggatg | 2700 |
| cggttgtttt caccgaggct ttcttggatg aatccggcgt ggatggcgca gacgaaggct | 2760 |
| gatgggcgtt tgtcgttg | 2778 |

<210> SEQ ID NO 7
<211> LENGTH: 1338
<212> TYPE: DNA
<213> ORGANISM: Artificial Sequence
<220> FEATURE:
<223> OTHER INFORMATION: R407H

<400> SEQUENCE: 7

| | |
|---|---|
| atgacctcag catctgcccc aagctttaac cccggcaagg gtcccggctc agcagtcgga | 60 |
| attgcccttt taggattcgg aacagtcggc actgaggtga tgcgtctgat gaccgagtac | 120 |
| ggtgatgaac ttgcgcaccg cattggtggc ccactggagg ttcgtggcat tgctgttttct | 180 |
| gatatctcaa agccacgtga aggcgttgca cctgagctgc tcactgagga cgcttttgca | 240 |
| ctcatcgagc gcgaggatgt tgacatcgtc gttgaggtta tcggcggcat tgagtaccca | 300 |
| cgtgaggtag ttctcgcagc tctgaaggcc ggcaagtctg ttgttaccgc caataaggct | 360 |
| cttgttgcag ctcactctgc tgagcttgct gatgcagcgg aagccgcaaa cgttgacctg | 420 |
| tacttcgagg ctgctgttgc aggcgcaatt ccagtggttg gcccactgcg tcgctccctg | 480 |
| gctggcgatc agatccagtc tgtgatgggc atcgttaacg gcaccaccaa cttcatcttg | 540 |
| gacgccatgg attccaccgg cgctgactat gcagattctt ggctgaggc aactcgtttg | 600 |
| ggttacgccg aagctgatcc aactgcagac gtcgaaggcc atgacgccgc atccaaggct | 660 |
| gcaattttgg catccatcgc tttccacacc cgtgttaccg cggatgatgt gtactgcgaa | 720 |
| ggtatcagca acatcagcgc tgccgacatt gaggcagcac agcaggcagg ccacaccatc | 780 |
| aagttgttgg ccatctgtga aagttcacc aacaaggaag aaagtcggc tatttctgct | 840 |
| cgcgtgcacc cgactctatt acctgtgtcc cacccactgg cgtcggtaaa caagtccttt | 900 |
| aatgcaatct tgttgaagc agaagcagct ggtcgcctga tgttctacgg aaacggtgca | 960 |
| ggtggcgcgc caaccgcgtc tgctgtgctt ggcgacgtcg ttggtgccgc acgaaacaag | 1020 |
| gtgcacggtg gccgtgctcc aggtgagtcc acctacgcta acctgccgat cgctgatttc | 1080 |
| ggtgagacca ccactcgtta ccacctcgac atggatgtgg aagatcgcgt gggggttttg | 1140 |
| gctgaattgg ctagcctgtt ctctgagcaa ggaatctccc tgcgtacaat ccgacaggaa | 1200 |
| gagcgcgatg atgatgcaca tctgatcgtg gtcacccact ctgcgctgga atctgatctt | 1260 |
| tcccgcaccg ttgaactgct gaaggctaag cctgttgtta aggcaatcaa cagtgtgatc | 1320 |
| cgcctcgaaa gggactaa | 1338 |

<210> SEQ ID NO 8
<211> LENGTH: 445
<212> TYPE: PRT
<213> ORGANISM: Artificial Sequence
<220> FEATURE:

<223> OTHER INFORMATION: homoserine dehydrogenase R407H

<400> SEQUENCE: 8

```
Met Thr Ser Ala Ser Ala Pro Ser Phe Asn Pro Gly Lys Gly Pro Gly
1               5                   10                  15
Ser Ala Val Gly Ile Ala Leu Leu Gly Phe Gly Thr Val Gly Thr Glu
            20                  25                  30
Val Met Arg Leu Met Thr Glu Tyr Gly Asp Glu Leu Ala His Arg Ile
        35                  40                  45
Gly Gly Pro Leu Glu Val Arg Gly Ile Ala Val Ser Asp Ile Ser Lys
    50                  55                  60
Pro Arg Glu Gly Val Ala Pro Glu Leu Leu Thr Glu Asp Ala Phe Ala
65                  70                  75                  80
Leu Ile Glu Arg Glu Asp Val Asp Ile Val Glu Val Ile Gly Gly
                85                  90                  95
Ile Glu Tyr Pro Arg Glu Val Val Leu Ala Ala Leu Lys Ala Gly Lys
                100                 105                 110
Ser Val Val Thr Ala Asn Lys Ala Leu Val Ala Ala His Ser Ala Glu
            115                 120                 125
Leu Ala Asp Ala Ala Glu Ala Ala Asn Val Asp Leu Tyr Phe Glu Ala
        130                 135                 140
Ala Val Ala Gly Ala Ile Pro Val Val Gly Pro Leu Arg Arg Ser Leu
145                 150                 155                 160
Ala Gly Asp Gln Ile Gln Ser Val Met Gly Ile Val Asn Gly Thr Thr
                165                 170                 175
Asn Phe Ile Leu Asp Ala Met Asp Ser Thr Gly Ala Asp Tyr Ala Asp
                180                 185                 190
Ser Leu Ala Glu Ala Thr Arg Leu Gly Tyr Ala Glu Ala Asp Pro Thr
            195                 200                 205
Ala Asp Val Glu Gly His Asp Ala Ala Ser Lys Ala Ala Ile Leu Ala
        210                 215                 220
Ser Ile Ala Phe His Thr Arg Val Thr Ala Asp Asp Val Tyr Cys Glu
225                 230                 235                 240
Gly Ile Ser Asn Ile Ser Ala Ala Asp Ile Glu Ala Ala Gln Gln Ala
                245                 250                 255
Gly His Thr Ile Lys Leu Leu Ala Ile Cys Glu Lys Phe Thr Asn Lys
                260                 265                 270
Glu Gly Lys Ser Ala Ile Ser Ala Arg Val His Pro Thr Leu Leu Pro
            275                 280                 285
Val Ser His Pro Leu Ala Ser Val Asn Lys Ser Phe Asn Ala Ile Phe
        290                 295                 300
Val Glu Ala Glu Ala Ala Gly Arg Leu Met Phe Tyr Gly Asn Gly Ala
305                 310                 315                 320
Gly Gly Ala Pro Thr Ala Ser Ala Val Leu Gly Asp Val Val Gly Ala
                325                 330                 335
Ala Arg Asn Lys Val His Gly Gly Arg Ala Pro Gly Glu Ser Thr Tyr
                340                 345                 350
Ala Asn Leu Pro Ile Ala Asp Phe Gly Glu Thr Thr Thr Arg Tyr His
            355                 360                 365
Leu Asp Met Asp Val Glu Asp Arg Val Gly Val Leu Ala Glu Leu Ala
        370                 375                 380
Ser Leu Phe Ser Glu Gln Gly Ile Ser Leu Arg Thr Ile Arg Gln Glu
385                 390                 395                 400
```

-continued

Glu Arg Asp Asp Asp Ala His Leu Ile Val Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
        435                 440                 445

<210> SEQ ID NO 9
<211> LENGTH: 34
<212> TYPE: DNA
<213> ORGANISM: Artificial Sequence
<220> FEATURE:
<223> OTHER INFORMATION: primer

<400> SEQUENCE: 9
tcgagctcgg taccccctgcg acagcatgga actc                     34

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10
ctctagagga tccccttagt ccctttcgag gcgg                      34

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
caccggcgct gactatgc                                        18

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
tgggtgacca cgatcagat                                       19

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13 ttagtcccctt tcgaggcg                                       18

<210> SEQ ID NO 14
<211> LENGTH: 421
<212> TYPE: PRT
<213> ORGANISM: Artificial Sequence
<220> FEATURE:
<223> OTHER INFORMATION: lysC(L377K)

<400> SEQUENCE: 14

```
Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
            35                  40                  45

Glu Leu Leu Glu Leu Ala Ala Val Asn Pro Val Pro Pro Ala Arg
50                      55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
            115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
            195                 200                 205

Ser Lys Ile Leu Val Leu Arg Ser Val Glu Tyr Ala Arg Ala Phe Asn
            210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
            290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
            355                 360                 365

Arg Asp Val Asn Val Asn Ile Glu Lys Ile Ser Thr Ser Glu Ile Arg
            370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
```

420

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
tcgagctcgg tacccgctgc gcagtgttga atac        34

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
tggaaatctt ttcgatgttc acgttgacat        30

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
atgtcaacgt gaacatcgaa aagatttcca        30

<210> SEQ ID NO 18
<211> LENGTH: 34
<212> TYPE: DNA
<213> ORGANISM: Artificial Sequence
<220> FEATURE:
<223> OTHER INFORMATION: Primer

<400> SEQUENCE: 18
ctctagagga tccccgttca cctcagagac gatt        34

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
acggatccca gactccaaag caaaagcg        28

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
acaccacggc agaaccaggt gcaaaggaca        30

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
ctggttctgc cgtggtgtgc atcatctctg        30

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
acggatccaa ccaaacttgc tcacactc        28

<210> SEQ ID NO 23
<211> LENGTH: 1161
<212> TYPE: DNA
<213> ORGANISM: Artificial Sequence
<220> FEATURE:
<223> OTHER INFORMATION: metB gene

<400> SEQUENCE: 23
ttgtcttttg acccaaacac ccagggtttc tccactgcat cgattcacgc tgggtatgag        60
ccagacgact actacggttc gattaacacc ccaatctatg cctccaccac cttcgcgcag       120
aacgctccaa acgaactgcg caaaggctac gagtacaccc gtgtgggcaa ccccaccatc       180
gtggcattag agcagaccgt cgcagcactc gaaggcgcaa agtatggccg cgcattctcc       240
tccggcatgg ctgcaaccga catcctgttc cgcatcatcc tcaagccggg cgatcacatc       300
gtcctcggca acgatgctta cggcggaacc taccgcctga tcgacaccgt attcaccgca       360
tggggcgtcg aatacaccgt tgttgatacc tccgtcgtgg aagaggtcaa ggcagcgatc       420
aaggacaaca ccaagctgat ctgggtggaa accccaacca acccagcact tggcatcacc       480
gacatcgaag cagtagcaaa gctcaccgaa ggcaccaacg ccaagctggt tgttgacaac       540
accttcgcat ccccatacct gcagcagcca ctaaaactcg gcgcacacgc agtcctgcac       600
tccaccacca agtacatcgg aggacactcc gacgttgttg gcggccttgt ggttaccaac       660
gaccaggaaa tggacgaaga actgctgttc atgcagggcg gcatcggacc gatcccatca       720
gttttcgatg catacctgac cgcccgtggc ctcaagaccc ttgcagtgcg catggatcgc       780
cactgcgaca acgcagaaaa gatcgcggaa ttcctggact cccgcccaga ggtctccacc       840
gtgctctacc caggtctgaa gaaccaccca ggccacgaag tcgcagcgaa gcagatgaag       900
cgcttcggcg gcatgatctc cgtccgtttc gcaggcggcg aagaagcagc taagaagttc       960
tgtacctcca ccaaactgat ctgtctggcc gagtccctcg gtggcgtgga atccctcctg      1020
gagcacccag caaccatgac ccaccagtca gctgccggct ctcagctcga ggttccccgc      1080
gacctcgtgc gcatctccat tggtattgaa gacattgaag acctgctcgc agatgtcgag      1140
caggccctca ataacctttta g                                              1161

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24

```
tctagacgcc cgcatactgg cttc                                              24
```

<210> SEQ ID NO 25
<211> LENGTH: 37
<212> TYPE: DNA
<213> ORGANISM: Artificial Sequence
<220> FEATURE:
<223> OTHER INFORMATION: Primer

<400> SEQUENCE: 25

```
cccatccact aaacttaaac agatgtgatc gcccggc                                37
```

<210> SEQ ID NO 26
<211> LENGTH: 38
<212> TYPE: DNA
<213> ORGANISM: Artificial Sequence
<220> FEATURE:
<223> OTHER INFORMATION: Primer

<400> SEQUENCE: 26

```
tgtttaagtt tagtggatgg ggaagaacca cccaggcc                               38
```

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27

```
gtcgaccaat cgtccagagg gcg                                               23
```

<210> SEQ ID NO 28
<211> LENGTH: 1314
<212> TYPE: DNA
<213> ORGANISM: Artificial Sequence
<220> FEATURE:
<223> OTHER INFORMATION: metY gene

<400> SEQUENCE: 28

```
atgccaaagt acgacaattc caatgctgac cagtggggct tgaaaccccg ctccattcac       60
gcaggccagt cagtagacgc acagaccagc gcacgaaacc ttccgatcta ccaatccacc      120
gctttcgtgt tcgactccgc tgagcacgcc aagcagcgtt tcgcacttga ggatctaggc      180
cctgtttact cccgcctcac caacccaacc gttgaggctt tggaaaaccg catcgcttcc      240
ctcgaaggtg gcgtccacgc tgtagcgttc tcctccggac aggccgcaac caccaacgcc      300
attttgaacc tggcaggagc gggcgaccac atcgtcacct ccccacgcct ctacggtggc      360
accgagactc tattccttat cactcttaac cgcctgggta tcgatgtttc cttcgtggaa      420
aaccccgacg accctgagtc ctggcaggca gccgttcagc aaacaccaa agcattcttc       480
ggcgagactt cgccaacccc acaggcagac gtcctggata ttcctgcggt ggctgaagtt      540
gcgcaccgca acagcgttcc actgatcatc gacaacacca tcgctaccgc agcgctcgtg      600
cgcccgctcg agctcggcgc agacgttgtc gtcgcttccc tcaccaagtt ctacaccggc      660
aacggctccg gactgggcgg cgtgcttatc gacgcggaa agttcgattg gactgtcgaa      720
aaggatggaa agccagtatt cccctacttc gtcactccag atgctgctta ccacggattg      780
aagtacgcag accttggtgc accagccttc ggcctcaagg ttcgcgttgg ccttctacgc      840
gacaccggct ccaccctctc cgcattcaac gcatgggctg cagtccaggg catcgacacc      900
ctttccctgc gcctggagcg ccacaacgaa aacgccatca aggttgcaga attcctcaac      960
```

```
aaccacgaga aggtggaaaa ggttaacttc gcaggcctga aggattcccc ttggtacgca      1020
accaaggaaa agcttggcct gaagtacacc ggctccgttc tcaccttcga gatcaagggc      1080
ggcaaggatg aggcttgggc atttatcgac gccctgaagc tacactccaa ccttgcaaac      1140
atcggcgatg ttcgctccct cgttgttcac ccagcaacca ccaccccattc acagtccgac     1200 gaagctggcc tggcacgcgc gggcgttacc cagtccaccg tccgcctgtc cgttggcatc      1260
gagaccattg atgatatcat cgctgacctc gaaggcggct ttgctgcaat ctag            1314
```

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29

```
tctagaccat cctgcaccat ttag                                              24
```

<210> SEQ ID NO 30
<211> LENGTH: 37
<212> TYPE: DNA
<213> ORGANISM: Artificial Sequence
<220> FEATURE:
<223> OTHER INFORMATION: Primer

<400> SEQUENCE: 30

```
cccatccact aaacttaaac acgctcctgc caggttc                                37
```

<210> SEQ ID NO 31
<211> LENGTH: 39
<212> TYPE: DNA
<213> ORGANISM: Artificial Sequence
<220> FEATURE:
<223> OTHER INFORMATION: Primer

<400> SEQUENCE: 31

```
tgtttaagtt tagtggatgg gcttggtacg caaccaagg                              39
```

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32

```
gtcgacgatt gctccggctt cgg                                               23
```

<210> SEQ ID NO 33
<211> LENGTH: 2213
<212> TYPE: DNA
<213> ORGANISM: Artificial Sequence
<220> FEATURE:
<223> OTHER INFORMATION: mcbR gene

<400> SEQUENCE: 33

```
aatctggatt tccgccaggt tttggcacgc ccgtctggtt taggcaatga gataccgaac        60
acacgtgcca aaagttcggc ttttttcgccg atcttgtcac gcctgcctgg tttgtcttgt      120
aaagagtgat ttcatggccg agactcctaa aagtttgacc tcacaggatt gcttctaagg      180
gcctctccaa tctccactga ggtacttaat ccttccgggg aattcgggcg cttaaatcga      240
```

```
gaaattaggc catcacctttt taataacaat acaatgaata attggaatag gtcgacacct    300
ttggagcgga gccggttaaa attggcagca ttcaccgaaa gaaaggaga accacatgct     360 tgccctaggt tggattacat ggatcattat tggtggtcta gctggttgga ttgcctccaa   420
gattaaaggc actgatgctc agcaaggaat tttgctgaac atagtcgtcg gtattatcgg   480
tggtttgtta ggcggctggc tgcttggaat cttcggagtg gatgttgccg gtggcggctt   540
gatcttcagc ttcatcacat gtctgattgg tgctgtcatt ttgctgacga tcgtgcagtt   600
cttcactcgg aagaagtaat ctgctttaaa tccgtagggc ctgttgatat ttcgatatca   660
acaggccttt tggtcatttt ggggtggaaa aagcgctaga cttgcctgtg gattaaaact   720
atacgaaccg gtttgtctat attggtgtta gacagttcgt cgtatcttga aacagaccaa   780
cccgaaagga cgtggccgaa cgtggctgct agcgcttcag gcaagagtaa aacaagtgcc   840
ggggcaaacc gtcgtcgcaa tcgaccaagc ccccgacagc gtctcctcga tagcgcaacc   900
aaccttttca ccacagaagg tattcgcgtc atcggtattg atcgtatcct ccgtgaagct   960
gacgtggcga aggcgagcct ctattccctt ttcggatcga aggacgcctt ggttattgca  1020
tacctggaga acctcgatca gctgtggcgt gaagcgtggc gtgagcgcac cgtcggtatg  1080
aaggatccgg aagataaaat catcgcgttc tttgatcagt gcattgagga agaaccagaa  1140
aaagatttcc gcggctcgca ctttcagaat gcggctagtg agtaccctcg ccccgaaact  1200
gatagcgaaa agggcattgt tgcagcagtg ttagagcacc gcgagtggtg tcataagact  1260
ctgactgatt tgctcactga gaagaacggc tacccaggca ccacccaggc gaatcagctg  1320
ttggtgttcc ttgatggtgg acttgctgga tctcgattgg tccacaacat cagtcctctt  1380
gagacggctc gcgatttggc tcggcagttg ttgtcggctc cacctgcgga ctactcaatt  1440
tagtttcttc attttccgaa ggggtatctt cgttgggggga ggcgtcgata agcccccttct 1500 ttttagcttt aacctcagcg cgacgctgct ttaagcgctg catggcggcg cggttcattt  1560
cacgttgcgt ttcgcgcctc ttgttcgcga tttctttgcg ggcctgtttt gcttcgttga  1620
tttcggcagt acgggttttg gtgagttcca cgtttgttgc gtgaagcgtt gaggcgttcc  1680
atggggtgag aatcatcagg gcgcggtttt tgcgtcgtgt ccacaggaag atgcgctttt  1740 cttttttgttt tgcgcggtag atgtcgcgct gctctaggtg gtgcactttg aaatcgtcgg  1800
taagtgggta tttgcgttcc aaaatgacca tcatgatgat tgtttggagg agcgtccaca  1860
ggttgttgct gacccaatag agtgcgattg ctgtggggaa tggtcctgtg aggccaaggg  1920
acagtgggaa gatcggcgcg aggatcgaca tcacgatcat gaacttcagc atgccgttag  1980
agaatccgga tgcgtaatcg ttggtttgga agctgcggta catggacatc gccatgttga  2040
ttgcggtgag gattgcggct gtgatgaaca gtggcaaaac gaaactaaga acttccgcct  2100
gcgtggtgct caaatatttt agctgctcag tgggcatcga aacataagcg ggcagaggca  2160
cattgctcac gcgaccagcg aggaaagatt ccacttcctc aggagttagg aag          2213
```

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
ggcccgggcc tgcctggttt gtcttgta                                        28

<210> SEQ ID NO 35
<211> LENGTH: 35
<212> TYPE: DNA
<213> ORGANISM: Artificial Sequence
<220> FEATURE:
<223> OTHER INFORMATION: Primer

<400> SEQUENCE: 35
cggaaaatga agaaagttcg gccacgtcct ttcgg    35

<210> SEQ ID NO 36
<211> LENGTH: 35
<212> TYPE: DNA
<213> ORGANISM: Artificial Sequence
<220> FEATURE:
<223> OTHER INFORMATION: Primer

<400> SEQUENCE: 36
aggacgtggc cgaactttct tcattttccg aaggg    35

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
atcccggggt ttcgatgccc actgagca    28

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
aatctggatt tccgccaggt    20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
cttcctaact cctgaggaag    20

<210> SEQ ID NO 40
<211> LENGTH: 445
<212> TYPE: PRT
<213> ORGANISM: Artificial Sequence
<220> FEATURE:
<223> OTHER INFORMATION: homoserine dehydrogenase (ATCC14067)

<400> SEQUENCE: 40

Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
            20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Val Ser Asp Ile Ser Lys

```
            50                  55                  60
Pro Arg Glu Gly Val Ala Pro Glu Leu Leu Thr Glu Asp Ala Phe Ala
 65                  70                  75                  80

Leu Ile Glu Arg Glu Asp Val Asp Ile Val Glu Val Ile Gly Gly
                 85                  90                  95

Ile Glu Tyr Pro Arg Glu Val Val Leu Ala Ala Leu Lys Ala Gly Lys
            100                 105                 110

Ser Val Val Thr Ala Asn Lys Ala Leu Val Ala Ala His Ser Ala Glu
            115                 120                 125

Leu Ala Asp Ala Ala Glu Ala Ala Asn Val Asp Leu Tyr Phe Glu Ala
130                 135                 140

Ala Val Ala Gly Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
            180                 185                 190

Ser Leu Ala Glu Ala Thr Arg Leu Gly Tyr Ala Glu Ala Asp Pro Thr
            195                 200                 205

Ala Asp Val Glu Gly His Asp Ala Ala Ser Lys Ala Ala Ile Leu Ala
210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
            260                 265                 270

Glu Gly Lys Ser Ala Ile Ser Ala Arg Val His Pro Thr Leu Leu Pro
            275                 280                 285

Val Ser His Pro Leu Ala Ser Val Asn Lys Ser Phe Asn Ala Ile Phe
290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Arg Ala Pro Gly Glu Ser Thr Tyr
            340                 345                 350

Ala Asn Leu Pro Ile Ala Asp Phe Gly Glu Thr Thr Thr Arg Tyr His
            355                 360                 365

Leu Asp Met Asp Val Glu Asp Arg Val Gly Val Leu Ala Glu Leu Ala
370                 375                 380

Ser Leu Phe Ser Glu Gln Gly Ile Ser Leu Arg Thr Ile Arg Gln Glu
385                 390                 395                 400

Glu Arg Asp Asp Ala Arg Leu Ile Val Thr His Ser Ala Leu
                405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
            435                 440                 445

<210> SEQ ID NO 41
<211> LENGTH: 445
<212> TYPE: PRT
<213> ORGANISM: Artificial Sequence
```

<220> FEATURE:
<223> OTHER INFORMATION: homoserine dehydrogenase (ATCC13869)

<400> SEQUENCE: 41

```
Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
            20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Val Ser Asp Ile Ser Lys
    50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Glu Val Ile Gly Gly
                85                  90                  95

Ile Glu Tyr Pro Arg Glu Val Val Leu Ala Ala Leu Lys Ala Gly Lys
                100                 105                 110

Ser Val Val Thr Ala Asn Lys Ala Leu Val Ala Ala His Ser Ala Glu
            115                 120                 125

Leu Ala Asp Ala Ala Glu Ala Ala Asn Val Asp Leu Tyr Phe Glu Ala
    130                 135                 140

Ala Val Ala Ala Ile Pro Val Val Gly Pro Leu Arg Arg Ser Leu
145                 150                 155                 160

Ala Gly Asp Gln Ile Gln Ser Val Met Gly Ile Val Asn Gly Thr Thr
                165                 170                 175

Asn Phe Ile Leu Asp Ala Met Asp Ser Thr Gly Ala Asp Tyr Ala Asp
                180                 185                 190

Ser Leu Ala Glu Ala Thr Arg Leu Gly Tyr Ala Glu Ala Asp Pro Thr
            195                 200                 205

Ala Asp Val Glu Gly His Asp Ala Ala Ser Lys Ala Ala Ile Leu Ala
    210                 215                 220

Ser Ile Ala Phe His Thr Arg Val Thr Ala Asp Asp Val Tyr Cys Glu
225                 230                 235                 240

Gly Ile Ser Asn Ile Ser Ala Ala Asp Ile Glu Ala Ala Gln Gln Ala
                245                 250                 255

Gly His Thr Ile Lys Leu Leu Ala Ile Cys Glu Lys Phe Thr Asn Lys
                260                 265                 270

Glu Gly Lys Ser Ala Ile Ser Ala Arg Val His Pro Thr Leu Leu Pro
            275                 280                 285

Val Ser His Pro Leu Ala Ser Val Asn Lys Ser Phe Asn Ala Ile Phe
    290                 295                 300

Val Glu Ala Glu Ala Ala Gly Arg Leu Met Phe Tyr Gly Asn Gly Ala
305                 310                 315                 320

Gly Gly Ala Pro Thr Ala Ser Ala Val Leu Gly Asp Val Val Gly Ala
                325                 330                 335

Ala Arg Asn Lys Val His Gly Gly Arg Ala Pro Gly Glu Ser Thr Tyr
                340                 345                 350

Ala Asn Leu Pro Ile Ala Asp Phe Gly Glu Thr Thr Thr Arg Tyr His
            355                 360                 365

Leu Asp Met Asp Val Glu Asp Arg Val Gly Val Leu Ala Glu Leu Ala
    370                 375                 380

Ser Leu Phe Ser Glu Gln Gly Ile Ser Leu Arg Thr Ile Arg Gln Glu
385                 390                 395                 400
```

```
Glu Arg Asp Asp Asp Ala Arg Leu Ile Val Val Thr His Ser Ala Leu
            405                 410                 415

Glu Ser Asp Leu Ser Arg Thr Val Glu Leu Leu Lys Ala Lys Pro Val
            420                 425                 430

Val Lys Ala Ile Asn Ser Val Ile Arg Leu Glu Arg Asp
            435                 440                 445
```

MODIFIED HOMOSERINE DEHYDROGENASE AND METHOD FOR PRODUCING HOMOSERINE OR L-AMINO ACID DERIVED FROM HOMOSERINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_448USPC_SEQUENCE_LISTING.txt. The text file is 36.7 KB, was created on Jul. 7, 2019, and is being submitted electronically via EFS-Web.

TECHNICAL FIELD

The present disclosure relates to modified homoserine dehydrogenase, and specifically, to modified homoserine dehydrogenase having a polypeptide comprising one or more amino acid substitutions in an amino acid sequence of a protein having the activity of homoserine dehydrogenase, in which the amino acid substitution is comprising substitution of the amino acid at position 407 of the amino acid sequence with histidine; and a method for producing homoserine or a homoserine-derived L-amino acid using the modified homoserine dehydrogenase.

BACKGROUND ART

Among L-amino acids, L-threonine, L-isoleucine, and L-methionine commonly use homoserine produced by homoserine dehydrogenase (hereinafter, "Hom"; EC:1.1.1.3) from aspartate-semialdehyde (hereinafter, "ASA"). Therefore, to produce the amino acids by a fermentation method, it is essential to maintain the activities of enzymes used in the biosynthetic pathway at a certain level or higher, and intensive research has been conducted thereon.

In particular, the activity of homoserine dehydrogenase acting at the branch point of the biosynthetic pathways of L-lysine and L-methionine is known to be regulated by L-threonine and L-isoleucine. Recently, there have been several reports on Hom desensitized to feedback inhibition by L-threonine and a method for producing L-threonine using the same. In 1991, Eikmann et al. in Germany reported Hom desensitized by substituting glycine, which is the amino acid residue at position 378 of Hom, with glutamate (Eikmanns B J et al., Appl. Microbial Biotechnol. 34: 617-622, 1991); and in 1991, Archer et al. reported that desensitization occurs when the C-terminus of Hom is damaged due to a frame-shift mutation (Archer J A et al., Gene 107: 53-59, 1991).

DISCLOSURE

Technical Problem

The present inventors have conducted a study on desensitization to feedback inhibition by threonine, and as a result, they have isolated a novel gene encoding modified Hom and confirmed that the L-amino acid-producing ability is improved in a microorganism where the novel gene is transduced, thereby completing the present disclosure.

Technical Solution

An object of the present invention is to provide modified homoserine dehydrogenase, in which in an amino acid sequence of a protein having the activity of homoserine dehydrogenase, the amino acid at position 407 of the amino acid sequence is substituted with histidine.

Another object of the present invention is to provide a polynucleotide encoding the modified dehydrogenase.

Still another object of the present invention is to provide a microorganism of the genus *Corynebacterium*, comprising the modified homoserine dehydrogenase.

Still another object of the present invention is to provide a method for producing homoserine or a homoserine-derived L-amino acid, which comprises culturing the microorganism in a medium; and recovering homoserine or a homoserine-derived L-amino acid from the cultured microorganism or cultured medium.

Still another object of the present invention is to provide a method for increasing the production of homoserine or a homoserine-derived L-amino acid in a microorganism, comprising enhancing the activity of the modified homoserine dehydrogenase.

Still another object of the present invention is to provide a use of the modified homoserine dehydrogenase for increasing the production of homoserine or a homoserine-derived L-amino acid.

Advantageous Effects

The modified homoserine dehydrogenase of the present disclosure can be widely used for efficient mass production of homoserine or a homoserine-derived L-amino acid because feedback inhibition by a final product is desensitized compared to the natural or wild type.

BEST MODE FOR CARRYING OUT THE INVENTION

Hereinbelow, the present disclosure will be described in detail. Meanwhile, each of the explanations and exemplary embodiments disclosed herein can be applied to other explanations and exemplary embodiments. That is, all combinations of various factors disclosed herein fall within the scope of the present disclosure. Further, the scope of the present disclosure should not be limited by the specific description provided hereinbelow.

In order to achieve the above objects, an aspect of the present disclosure provides modified homoserine dehydrogenase having a polypeptide comprising one or more amino acid substitutions in an amino acid sequence of a protein having the activity of homoserine dehydrogenase, in which the amino acid substitution is comprising substitution of the amino acid at position 407 of the amino acid sequence with another amino acid.

Specifically, the present disclosure provides modified homoserine dehydrogenase having a polypeptide comprising one or more amino acid substitutions in an amino acid sequence of a protein having the activity of homoserine dehydrogenase, in which the amino acid substitution is comprising substitution of the amino acid at position 407 of the amino acid sequence with histidine. More specifically, the present disclosure provides modified homoserine dehydrogenase, in which the amino acid at position 407 of the amino acid sequence of SEQ ID NO: 1 is substituted with histidine.

In the present disclosure, homoserine dehydrogenase (EC: 1.1.1.3) refers to an enzyme that catalyzes the synthesis of homoserine, which is a common intermediate for the biosynthesis of methionine, threonine, and isoleucine in plants and microorganisms. In the present disclosure, homoserine dehydrogenase may be included regardless of its origin as long as it has the above conversion activity, and an enzyme derived from any organism (plants, microorganisms, etc.) may be used as the homoserine dehydrogenase. Specifically, the homoserine dehydrogenase may be derived from a microorganism of the genus *Corynebacterium*, and more specifically may be derived from *Corynebacterium glutamicum*. For example, the homoserine dehydrogenase may be a protein including the amino acid sequence of SEQ ID NO: 1. The protein including the amino acid sequence of SEQ ID NO: 1 may be used interchangeably with the term "protein having the amino acid sequence of SEQ ID NO: 1" or "protein consisting of the amino acid sequence of SEQ ID NO: 1".

In the present disclosure, various methods well known in the art may be used as the method for obtaining homoserine dehydrogenase. Examples of such methods may include gene synthesis techniques including optimization of codons so as to obtain proteins at high efficiency in a microorganism of the genus *Corynebacterium*, which is commonly used for the expression of proteins, and methods for screening useful enzyme resources using bioinformatic methods based on the metagenomic information of microorganisms, but the methods are not limited thereto.

In the present disclosure, the protein having the activity of homoserine dehydrogenase does not exclude a mutation that can occur due to an addition of a nonsense sequence upstream or downstream of the amino acid sequence of a protein having the activity of homoserine dehydrogenase (e.g., the amino acid sequence of SEQ ID NO: 1), or a naturally occurring mutation, or a silent mutation therein. In addition, as long as the protein has activity the same as or corresponding to the protein including the amino acid sequence of SEQ ID NO: 1, the protein also corresponds to the protein having the activity of the homoserine dehydrogenase of the present disclosure. As a specific example, the protein having the activity of the homoserine dehydrogenase of the present disclosure may be a protein consisting of the amino acid sequence of SEQ ID NO: 1 or an amino acid sequence having a homology thereto of at least 80%, at least 90%, at least 95%, or at least 97%.

Additionally, although it is described as "protein or polypeptide including the amino acid sequence of a particular SEQ ID NO" in the present disclosure, it is apparent that any protein having an amino acid sequence with deletion, modification, substitution, or addition in part of the sequence can also belong to the scope of the present disclosure as long as the protein has an amino acid sequence with any of the above homologies and exhibits an effect corresponding to the above protein. For example, in the present disclosure, the protein having the activity of homoserine dehydrogenase may be homoserine dehydrogenase derived from *Corynebacterium glutamicum*. More specifically, the protein having the activity of homoserine dehydrogenase may be the amino acid sequence (SEQ ID NO: 1) of homoserine dehydrogenase derived from *Corynebacterium glutamicum* ATCC13032, the amino acid sequence (SEQ ID NO: 40) of homoserine dehydrogenase derived from *Corynebacterium glutamicum* ATCC14067, or the amino acid sequence (SEQ ID NO: 41) of homoserine dehydrogenase derived from *Corynebacterium glutamicum* ATCC13869. Since the homoserine dehydrogenases having the above sequences show a homology of at least 80%, at least 90%, at least 95%, or at least 97% or to one other, and since these homoserine dehydrogenases exhibit effects corresponding to those of homoserine dehydrogenase, it is apparent that they are included in the protein having the activity of the homoserine dehydrogenase of the present disclosure.

As used herein, the term "homology" refers to the percentage of identity between two polynucleotide or polypeptide moieties. The homology refers to a degree of matching with a given amino acid sequence or nucleotide sequence, and may be expressed as a percentage. In the present disclosure, a homology sequence having an activity which is identical or similar to the given amino acid sequence or nucleotide sequence is expressed as "% homology". The homology between sequences from one moiety to another may be determined by techniques known in the art. For example, the homology may be confirmed using standard software (i.e., BLAST 2.0) for calculating parameters (e.g., score, identity, and similarity) or by comparing sequences via Southern hybridization experiments. The appropriate hybridization conditions to be defined may be determined by a method known to those skilled in the art (e.g., J. Sambrook et al., Molecular Cloning, A Laboratory Manual, $2^{nd}$ Edition, Cold Spring Harbor Laboratory press, Cold Spring Harbor, N.Y., 1989; F. M. Ausubel et al., Current Protocols in Molecular Biology, John Wiley & Sons, Inc., New York).

As used herein, the term "modification", "modified", or "variant" refers to a culture or an individual that shows an inheritable or non-heritable alternation in one stabilized phenotype. Specifically, these terms may refer to a variant in which its activity is efficiently increased because one or more amino acids in the amino acid sequence corresponding to a protein having the activity of homoserine dehydrogenase are modified compared to that of the wild-type, a native type, or non-modified type; a variant in which feedback inhibition by isoleucine, threonine, or an analog or derivative thereof is released; or a variant in which the increase in activity and release of feedback inhibition are both achieved.

In the present disclosure, the term "modified homoserine dehydrogenase" may be used interchangeably with "homoserine dehydrogenase variant". Meanwhile, such variant may be non-naturally occurring.

Specifically, the modified homoserine dehydrogenase of the present disclosure may be a modified protein having a polypeptide comprising one or more amino acid substitutions in the amino acid sequence of a protein having the activity of homoserine dehydrogenase, in which the amino acid substitution is comprising substitution of the amino acid at position 407 of the amino acid sequence with histidine. The amino acid sequence of the protein having the activity of homoserine dehydrogenase is as described above, and may be, for example, the amino acid sequence of SEQ ID NO: 1. In addition, the "amino acid at position 407" may refer to the amino acid at the position corresponding to the $407^{th}$ amino acid from the N-terminus of the amino acid sequence of SEQ ID NO: 1, and specifically, may refer to the $407^{th}$ amino acid from the N-terminus of the amino acid sequence of SEQ ID NO: 1. The amino acid at position 407 may be one in which arginine is substituted with histidine. More specifically, the modified homoserine dehydrogenase of the present disclosure may be a protein including the amino acid sequence of SEQ ID NO: 8. In addition, the protein does not exclude a mutation that can occur due to an addition of a nonsense sequence upstream or downstream of the amino acid sequence, a naturally occurring mutation, or a silent mutation therein, and any protein that has the activity identical or corresponding to that of the modified homoserine dehydrogenase corresponds to the protein having the activity of the modified homoserine dehydrogenase of the present disclosure. As a specific example, the modified homoserine dehydrogenase of the present disclosure may be a protein consisting of the amino acid sequence of SEQ ID NO: 8, or a protein consisting of an amino acid sequence having a homology to the above amino acid sequence of at least 80%, at least 90%, at least 95%, or at least 97% while the 407$^{th}$ amino acid from the N-terminus of the amino acid sequence of SEQ ID NO: 1 is fixed.

Additionally, unlike the wild-type or native protein, or a non-modified protein having the activity of homoserine dehydrogenase, the modified homoserine dehydrogenase of the present disclosure may be one in which feedback inhibition by a final product (i.e., isoleucine, threonine, methionine, homoserine, or a derivative or analog thereof) is released or desensitized. As used herein, the term "feedback inhibition" means that a final product of metabolism prevents the earlier-stage reaction. Therefore, when the feedback inhibition of homoserine dehydrogenase is released or desensitized, the productivity of homoserine and that of a homoserine-derived L-amino acid can be improved compared to when the feedback inhibition is not released or desensitized.

The homoserine-derived L-amino acid refers to an L-amino acid which can be biosynthesized using L-homoserine as a precursor, and is not limited as long as it is a material that can be biosynthesized from L-homoserine. The homoserine-derived L-amino acid may include not only a homoserine-derived L-amino acid but also a derivative thereof. For example, the homoserine-derived L-amino acid may be L-threonine, L-isoleucine, O-acetyl-L-homoserine, O-succinyl-L-homoserine, O-phospho-L-homoserine, L-methionine, and/or glycine, but the homoserine-derived L-amino acid is not limited thereto. More specifically, the homoserine-derived L-amino acid may be L-threonine, L-isoleucine, O-acetyl-L-homoserine, O-succinyl-L-homoserine, and/or L-methionine, but the homoserine-derived L-amino acid is not limited thereto.

Another aspect of the present disclosure provides a polynucleotide encoding the modified homoserine dehydrogenase.

The homoserine dehydrogenase and variant (modified one) are as described above.

As used herein, the term "polynucleotide" refers to a nucleotide polymer composed of nucleotide monomers covalently bonded in a long chain (e.g., DNA or RNA strands having a predetermined or longer length), and more specifically, it refers to a polynucleotide fragment encoding the modified homoserine dehydrogenase. The polynucleotide encoding the modified protein of the present disclosure may be included without limitation as long as it has a polynucleotide sequence encoding the modified protein having the activity of the homoserine dehydrogenase of the present disclosure.

In the present disclosure, the polynucleotide encoding the amino acid sequence of the homoserine dehydrogenase variant may be specifically derived from a microorganism of the genus *Corynebacterium*, and more specifically derived from *Corynebacterium glutamicum*. However, the microorganism is not limited thereto.

Additionally, due to codon degeneracy or in consideration of the codons preferred in an organism in which the protein is to be expressed, in the polynucleotide encoding the protein, various modifications may be made in the coding region without changing an amino acid sequence of the protein. Specifically, the polynucleotide may be a polynucleotide including a polynucleotide sequence encoding the protein or a polynucleotide sequence having a homology to the above polynucleotide sequence of at least 80%, at least 90%, at least 95%, or at least 97%. In addition, it is apparent that a polynucleotide sequence with deletion, modification, substitution, or addition in part of the sequence can also belong to the scope of the present disclosure as long as it is a polynucleotide sequence encoding the protein having the above homologies and exhibiting an effect substantially the same as or corresponding to the above protein. The polynucleotide encoding the protein having the activity of the homoserine dehydrogenase of the present disclosure may have a polynucleotide sequence encoding the amino acid sequence of SEQ ID NO: 1. For example, the polynucleotide may have the polynucleotide sequence of SEQ ID NO: 2, but is not limited thereto. In addition, the polynucleotide encoding the modified homoserine dehydrogenase of the present disclosure may have a polynucleotide sequence encoding the polypeptide comprising one or more amino acid substitutions in the amino acid sequence of SEQ ID NO: 1, and specifically, may have a polynucleotide sequence encoding SEQ ID NO: 8. For example, the polynucleotide may have the polynucleotide sequence of SEQ ID NO: 7, but is not limited thereto.

Additionally, a probe that can be prepared from a known gene sequence, for example, any sequence which hybridizes with a sequence complementary to all or part of the polynucleotide sequence under stringent conditions to encode a protein having the activity of the homoserine dehydrogenase of the present disclosure, may be also included without limitation. The "stringent conditions" mean conditions under which specific hybridization between polynucleotides is allowed. Such conditions are specifically described in the literature (e.g., J. Sambrook et al., supra). The stringent conditions may include, for example, conditions under which genes having high homology, 80% or higher homology, specifically 90% or higher homology, more specifically 95% or higher homology, much more specifically 97% or higher homology, still much more specifically 99% or higher homology are hybridized with each other and genes having homology lower than the above homology are not hybridized with each other, or ordinary washing conditions of Southern hybridization (i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS). Hybridization requires that two polynucleotides contain complementary sequences, although mismatches between bases may occur depending on the stringency of the hybridization. The term "complementary" is used to describe the relationship between nucleotide bases that are hybridizable with each other. For example, with respect to DNA, adenosine is complementary to thymine and cytosine is complementary to guanine. Therefore, the present disclosure may also include an isolated nucleotide fragment complementary to the entire sequence as well as a nucleotide sequence substantially similar thereto. Specifically, the polynucleotide having homology may be detected using hybridization conditions including a hybridization step at a $T_m$ value of 55° C. under the above-described conditions. Further, the $T_m$ value may be 60° C., 63° C., or 65° C., but is not limited thereto, and may be appropriately controlled by those skilled in the art depending on the purpose thereof. The appropriate stringency for hybridizing polynucleotides depends on the length of the polynucleotides and the degree of complementation, and these variables are well known in the art (see Sambrook et al., supra, 9.50-9.51, 11.7-11.8).

Still another aspect of the present disclosure provides a microorganism comprising the modified homoserine dehydrogenase. Specifically, the present disclosure provides a microorganism of the genus *Corynebacterium* producing homoserine or a homoserine-derived L-amino acid, comprising the modified homoserine dehydrogenase.

The homoserine dehydrogenase and variant are as described above.

Specifically, the microorganism comprising the modified homoserine dehydrogenase of the present disclosure refers to a microorganism which inherently has the ability to produce homoserine or a homoserine-derived L-amino acid, or a microorganism to which the ability to produce homoserine or a homoserine-derived L-amino acid is imparted to its parent strain lacking the ability to produce homoserine or a homoserine-derived L-amino acid. Specifically, the microorganism comprising the homoserine dehydrogenase may be a microorganism capable of expressing modified homoserine dehydrogenase, in which the amino acid at position 407 of the amino acid sequence of SEQ ID NO: 1 is substituted with histidine, but the microorganism is not limited thereto. The microorganism may be a cell or microorganism, which includes a polynucleotide encoding the modified homoserine dehydrogenase or is capable of expressing a modified polypeptide by transformation with a vector that includes a polynucleotide encoding the modified homoserine dehydrogenase. For the purposes of the present disclosure, the host cell or microorganism may be any microorganism capable of producing homoserine or a homoserine-derived L-amino acid, which includes the modified polypeptide.

The microorganism comprising the modified homoserine dehydrogenase of the present disclosure has an improved ability to produce homoserine and a homoserine-derived L-amino acid compared to the wild-type or a microorganism including a protein having the activity of non-modified homoserine dehydrogenase. Therefore, homoserine and a homoserine-derived L-amino acid can be obtained in high yield from the microorganism comprising the modified homoserine dehydrogenase of the present disclosure.

In the present disclosure, the type of microorganism including the modified homoserine dehydrogenase is not particularly limited, but may be a microorganism of the genus *Enterobacter*, a microorganism of the genus *Escherichia*, a microorganism of the genus *Envinia*, a microorganism of the genus *Serratia*, a microorganism of the genus *Pseudomonas*, a microorganism of the genus *Providencia*, a microorganism of the genus *Corynebacterium*, or a microorganism of the genus *Brevibacterium*. More specifically, the microorganism may be a microorganism of the genus *Corynebacterium*.

In the present disclosure, the "microorganism of the genus *Corynebacterium*" may be specifically *Corynebacterium glutamicum, Corynebacterium ammoniagenes, Brevibacterium lactofermentum, Brevibacterium flavum, Corynebacterium thermoaminogenes, Corynebacterium efficiens*, etc., but the microorganism of the genus *Corynebacterium* is not limited thereto. More specifically, in the present disclosure, the microorganism of the genus *Corynebacterium* may be *Corynebacterium glutamicum*.

Meanwhile, the microorganism comprising the modified homoserine dehydrogenase may be a microorganism into which a vector including a polynucleotide encoding a homoserine dehydrogenase variant is introduced. Specifically, the introduction may be performed by transformation, but the method of introduction is not limited thereto.

As used herein, the term "vector" refers to a DNA construct including a nucleotide sequence of a polynucleotide encoding a target protein, in which the target protein is operably linked to a suitable control sequence so that the target protein can be expressed in an appropriate host. The control sequence may include a promoter capable of initiating transcription, any operator sequence for the control of the transcription, a sequence encoding an appropriate mRNA ribosome-binding domain, and a sequence controlling the termination of transcription and translation. The vector, after transformation into a suitable host cell, may be replicated or function irrespective of the host genome, or may be integrated into the host genome itself.

The vector used in the present disclosure is not particularly limited, as long as it is able to replicate in a host cell, and any vector known in the art may be used. Examples of conventional vectors may include a natural or recombinant plasmid, cosmid, virus, and bacteriophage. For example, pWE15, M13, MBL3, MBL4, IXII, ASHII, APII, t10, t11, Charon4A, Charon21A, etc. may be used as a phage vector or cosmid vector; and pBR type, pUC type, pBluescriptII type, pGEM type, pTZ type, pCL type, pET type, etc. may be used as a plasmid vector. Specifically, vectors pACYC177, pACYC184, pCL, pECCG117, pUC19, pBR322, pMW118, pCC1BAC, etc. may be used, but the vector is not limited thereto.

A vector usable in the present disclosure is not particularly limited, and any known expression vector may be used. In addition, a polynucleotide encoding a target protein may be inserted into the chromosome through a vector for chromosomal insertion. The insertion of the polynucleotide into the chromosome may be performed by any method known in the art (e.g., homologous recombination), but the method is not limited thereto. The vector may further include a selection marker so as to confirm the insertion of the polynucleotide into the chromosome. A selection marker is for screening the cells transformed with the vector, i.e., for determining whether the target polynucleotide molecule is inserted. The markers that provide selectable phenotypes (e.g., drug resistance, auxotrophy, resistance to cell toxic agents, or expression of surface proteins) may be used. In an environment treated with a selective agent, only the cells expressing the selection marker can survive, or cells may show different phenotypes, and thus the transformed cells can be selected through this method.

As used herein, the term "transformation" refers to the introduction of a vector including a polynucleotide encoding a target protein into a host cell in such a way that the protein encoded by the polynucleotide is expressed in the host cell. As long as the transformed polynucleotide can be expressed in the host cell, it does not matter whether the transformed polynucleotide is integrated into the chromosome of the host cell and placed therein or is located extrachromosomally. Further, the polynucleotide includes DNA and RNA encoding the target protein. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. The expression cassette may include a promoter operably linked to the polynucleotide, transcription terminator, ribosome binding site, or translation terminating signal. The expression cassette may be in the form of a self-replicable expression vector. In addition, the polynucleotide may be introduced into the host cell as is and operably linked to sequences required for expression in the host cell, but the introduction method of the polynucleotide is not limited thereto. The transformation method includes any method of introducing a polynucleotide into a cell, and it may be performed by selecting a suitable standard technique known in the art depending on a host cell. Examples of the method include electroporation, calcium phosphate ($Ca(H_2PO_4)_2$, $CaHPO_4$, or $Ca_3(PO_4)_2$) precipitation, calcium chloride ($CaCl_2$) precipitation, microinjection, a polyethyleneglycol (PEG) method, a DEAE-dextran method, a cationic liposome method, a lithium acetate-DMSO method, etc., but the transformation methods are not limited thereto.

Additionally, the term "operable linkage" means that a promoter sequence that initiates and mediates transcription of a polynucleotide encoding a target protein of the present disclosure is functionally linked to the polynucleotide sequence. The operable linkage may be prepared using a gene recombination technique known in the art, and site-specific DNA cleavage and linkage may be prepared using known restriction enzymes and ligases, but the methods of the operable linkage are not limited thereto.

The microorganism comprising the modified homoserine dehydrogenase may be one which has been transformed to include the modified homoserine dehydrogenase in a microorganism of the genus *Corynebacterium*. For example, the microorganism of the genus *Corynebacterium* may include a strain resistant to 2-amino-3-hydroxy-valerate (AHV); a strain producing L-threonine by substituting leucine (i.e., the amino acid at position 377 of aspartate kinase (lysC)), with lysine so as to resolve the feedback inhibition of lysC (i.e., the first important enzyme acting in the biosynthetic pathway of threonine); a strain producing L-isoleucine by substituting the amino acid at position 323 of ilvA gene, which encodes L-threonine dehydratase (i.e., the first enzyme acting in the biosynthetic pathway of isoleucine) in the strain producing L-threonine, with alanine (Appl. Enviro. Microbiol., December 1996, p. 4345-4351); a strain producing O-acetylhomoserine by inactivating O-acetylhomoserine (thiol)-lyase, which is involved in the degradation pathway of O-acetyl homoserine, and cystathionine gamma-synthase; or a strain producing methionine by inactivating transcriptional regulatory factors of methionine and cysteine, but the strains of the microorganism of the genus *Corynebacterium* are not limited thereto.

Still another aspect of the present disclosure provides a method for producing homoserine or a homoserine-derived L-amino acid, comprising: culturing the above-described microorganism in a medium.

The method for producing an L-amino acid may comprise recovering homoserine or a homoserine-derived L-amino acid from the cultured microorganism or cultured medium.

As described above, the microorganism may be a microorganism of the genus *Corynebacterium*, comprising the homoserine dehydrogenase variant of the present disclosure, and more specifically may be *Corynebacterium glutamicum*. In addition, the microorganism of the genus *Corynebacterium* or *Corynebacterium glutamicum* may be a microorganism producing homoserine or a homoserine-derived L-amino acid. The homoserine-derived L-amino acid may include not only a homoserine-derived L-amino acid but also a derivative thereof. For example, the homoserine-derived L-amino acid may be L-threonine, L-isoleucine, O-acetyl-L-homoserine, O-succinyl-L-homoserine, O-phospho-L-homoserine, L-methionine, and/or glycine, but the homoserine-derived L-amino acid is not limited thereto. More specifically, the homoserine-derived L-amino acid may be L-threonine, L-isoleucine, O-acetyl-L-homoserine, O-succinyl-L-homoserine, and/or L-methionine, but the homoserine-derived L-amino acid is not limited thereto.

The homoserine or homoserine-derived L-amino acid may be a culture medium of homoserine or a homoserine-derived L-amino acid, which is produced by the microorganism described in the present disclosure, or may be in a purified form. It is apparent to those skilled in the art that the homoserine or homoserine-derived L-amino acid includes not only itself but also a salt thereof.

The method for producing the homoserine or homoserine-derived L-amino acid may be easily determined by those skilled in the art under optimized culture conditions and enzyme activity conditions known in the art.

In the above method, the microorganism may be cultured in a batch process, continuous process, fed-batch process, etc. known in the art, but the culture process is not particularly limited thereto. In particular, with respect to the culture conditions, the pH of the culture may be adjusted to a suitable pH (e.g., pH 5 to pH 9, specifically pH 6 to pH 8, and most specifically pH 6.8) with an appropriate basic compound (e.g., sodium hydroxide, potassium hydroxide, or ammonia) or acidic compound (e.g., phosphoric acid or sulfuric acid), and the aerobic condition of the culture may be maintained by introducing oxygen or an oxygen-containing gas mixture to the culture. The culture temperature may generally be in a range of 20° C. to 45° C., and specifically 25° C. to 40° C. for about 10 to 160 hours, but the culture conditions are not limited thereto. The threonine, isoleucine, or acetyl homoserine produced by the culture process may be secreted into the culture or may be retained in the cells.

Additionally, as the carbon sources for the culture medium, sugar and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid); alcohols (e.g., glycerol and ethanol); organic acids (e.g., acetic acid); etc. may be used alone or in combination, but the carbon sources are not limited thereto. As the nitrogen sources for the culture medium, nitrogen-containing organic compounds (e.g., peptone, yeast extract, meat gravy, malt extract, corn steep liquor, soybean flour, and urea) or inorganic compounds (e.g., ammonium sulfate, ammonium chloride, ammonium phosphate, ammonium carbonate, and ammonium nitrate), etc. may be used alone or in combination, but the nitrogen sources are not limited thereto. As the phosphorus sources for the culture medium, potassium dihydrogen phosphate, dipotassium hydrogen phosphate, corresponding sodium-containing salts, etc. may be used alone or in combination, but the phosphorus sources are not limited thereto. Additionally, the medium may contain other metal salts (e.g., magnesium sulfate or iron sulfate), amino acids, vitamins, etc., which are essential growth-promoting materials.

In the present disclosure, the method for recovering the homoserine or homoserine-derived L-amino acid produced in the culture process may be performed by collecting the target product from the culture broth using an appropriate method known in the art. For example, methods such as centrifugation, filtration, anion-exchange chromatography, crystallization, HPLC, etc. may be used, and the target material, which is the homoserine or homoserine-derived L-amino acid, can be recovered from a cultured medium or cultured microorganism using an appropriate method known in the art. Further, the recovery may include an additional purification process and may be performed using an appropriate method known in the art.

Still another aspect of the present disclosure provides a use of the modified homoserine dehydrogenase for increasing the production of homoserine or a homoserine-derived L-amino acid.

Still another aspect of the present disclosure provides a method for increasing the production of homoserine or a homoserine-derived L-amino acid in a microorganism, comprising enhancing the activity of the modified homoserine dehydrogenase.

As used herein, the term "to be expressed/being expressed" refers to a state in which a target protein is introduced into a microorganism or, in the case where the protein is present in the microorganism, the activity of the protein is enhanced compared to the activity of its endogenous protein or that before its modification.

Specifically, the term "introduction of a protein" means that a microorganism exhibits the activity of a particular protein which was not originally possessed in the microorganism or the microorganism exhibits enhanced activity compared to its endogenous activity or the activity of the protein before modification. For example, it may mean that a polynucleotide encoding a particular protein is introduced into the chromosome of a microorganism or a vector containing a polynucleotide encoding a particular protein is introduced into a microorganism and thereby exhibits its activity. Additionally, the term "enhancement of activity" means that the activity of a particular protein is improved compared to its endogenous activity or the activity before its modification. The term "endogenous protein" refers to the activity of a particular protein originally possessed by a parent strain of a microorganism, in a case where a trait of a microorganism is altered due to genetic modification caused by a natural or artificial factor.

Specifically, in the present disclosure, the enhancement of activity may be achieved by one or more of the following methods: a method of increasing the intracellular copy number of a gene encoding the protein variant; a method of introducing a modification to the expression control sequence of a gene encoding the protein variant; a method of replacing the expression control sequence of a gene encoding the protein variant with a sequence having strong activity; a method of replacing a gene encoding the native protein on the chromosome having the homoserine dehydrogenase activity with a gene encoding the protein variant; a method of introducing a further modification into a gene encoding the protein having the homoserine dehydrogenase activity so as to enhance the activity of the protein variant; and a method of introducing the protein variant to a microorganism, but the methods are not limited thereto.

In the above, the copy number of a gene may be increased in a form where the gene is operably linked to a vector or by inserting the gene into the chromosome of a host cell, but the method is not particularly limited thereto. Specifically, the copy number of a gene may be increased by introducing a vector into a host cell, where the vector is operably linked to a polynucleotide encoding the protein of the present disclosure and is able to replicate and function regardless of the host cell. Alternatively, the copy number of a gene may be increased by introducing a vector, to which the polynucleotide is operably linked, into the chromosome of a host cell. The insertion of the polynucleotide into the chromosome may be achieved by a method known in the art (e.g., homologous recombination).

Then, to increase the expression of a polynucleotide, the expression control sequence may be modified by inducing a modification therein by deletion, insertion, non-conservative or conservative substitution, or a combination thereof so as to further enhance the activity of the expression control sequence; or by replacing the expression control sequence with a nucleic acid sequence with stronger activity, but the method of modification is not particularly limited thereto. The expression control sequence may include a promoter, an operator sequence, a sequence encoding a ribosome-binding site, sequences controlling the termination of transcription and translation, etc., but the expression control sequence is not limited thereto.

A strong promoter may be linked to the upstream region of the expression unit of the polynucleotide instead of the original promoter, but the method is not limited thereto. Examples of strong promoters known in the art may include cj 1 to cj7 promoters (KR Patent No. 10-0620092), lac promoter, trp promoter, trc promoter, tac promoter, lambda phage PR promoter, PL promoter, tet promoter, gapA promoter, SPL7 promoter, SPL13 (sm3) promoter (KR Patent No. 10-1783170), O2 promoter (KR Patent No. 10-1632642), tkt promoter, yccA promoter, etc., but the promoters are not limited thereto.

Further, the modification of the polynucleotide sequence on the chromosome may be performed by inducing a modification on the expression control sequence by deletion, insertion, non-conservative or conservative substitution, or a combination thereof so as to further enhance the activity of the polynucleotide sequence; or by replacing the polynucleotide sequence with a polynucleotide sequence modified to have stronger activity, but the method of modification is not particularly limited thereto.

The introduction and enhancement of protein activity as described above may generally increase the activity or concentration of the corresponding protein by at least 1%, at least 10%, at least 25%, at least 50%, at least 75%, at least 100%, at least 150%, at least 200%, at least 300%, at least 400%, or at least 500%, and at most 1,000% or 2,000%, based on the activity or concentration of the protein in a wild-type or non-modified microorganism strain, but the range is not limited thereto.

The amino acid sequence of the protein having the activity of homoserine dehydrogenase, the amino acid at position 407, and microorganism are as described above.

DETAILED DESCRIPTION OF THE INVENTION

Hereinafter, the present disclosure will be described in detail through exemplary embodiments. However, these exemplary embodiments are for illustrative purposes only and are not intended to limit the scope of the present disclosure.

Example 1: Screening for AHV-Resistant Microorganisms Through Artificial Modification In this Example, an experiment of imparting resistance against 2-amino-3-hydroxy-valerate (hereinafter, "AHV"), which is an L-threonine analog, was conducted using *Corynebacterium glutamicum* KFCC10881 (KR Patent No. 0159812) as a parent strain, so as to release the feedback inhibition by L-threonine of homoserine dehydrogenase (hereinafter, "Hom", EC:1.1.1.3).

Modification was induced by an artificial modification method using N-methyl-N'-nitro-N-nitrosoguanidine (hereinafter, "NTG"). The KFCC10881 strain, which had been cultured in a seed medium for 18 hours, was inoculated into 4 mL of the seed medium, and then cultured until $OD_{660}$ reached about 1.0. The culture medium was centrifuged to recover the cells, and then the cells were washed twice with a 50 mM Tris-malate buffer (pH 6.5) and suspended in the final 4 mL of the same buffer. An NTG solution (2 mg/mL in a 0.05 M Tris-malate buffer (pH 6.5)) was added to the cell suspension to have a final concentration of 150 mg/L, and then allowed to stand at room temperature for 20 minutes. Thereafter, the cells were recovered by centrifugation, and washed twice with the same buffer to remove the NTG. The finally washed cells were suspended in 4 mL of a 20% glycerol solution and then stored at −70° C. until use. The NTG-treated strains were plated on a minimal medium containing 3 g/L of AHV, and then 126 AHV-resistant strains derived from KFCC10881 were obtained through the above procedure.

Seed Medium (pH 7.0)

glucose 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100 µg, thiamine HCl 1,000 µg, calcium pantothenate 2,000 µg, nicotinamide 2,000 µg (based on 1 L of distilled water)

Minimal Medium (pH 7.2)

glucose 5 g, $KH_2PO_4$ 1 g, $(NH_4)_2SO_4$ 5 g, $MgSO_4$ $7H_2O$ 0.4 g, NaCl 0.5 g, biotin 200 µg, thiamine HCl 100 µg, calcium pantothenate 100 µg, nicotinamide 0.03 g, urea 2 g, $Na_2B_4O_7$ $10H_2O$ 0.09 mg, $(NH_4)_6Mo_7O_{27}$ $4H_2O$ 0.04 mg, $ZnSO_4$ $7H_2O$ 0.01 mg, $CuSO_4$ $5H_2O$, $MnCl_2$ $4H_2O$ 0.01 mg, $FeCl_3$ $6H_2O$ 1 mg, $CaCl_2$ 0.01 mg (based on 1 L of distilled water)

Example 2: L-Threonine Production Test for AHV-Resistant Strain Derived from KFCC10881

A test for the L-threonine-producing ability was conducted on the 126 AHV-resistant strains obtained in Example 1. The 126 strains obtained in Example 1 were inoculated into each corner-baffled flask (250 mL) containing the seed medium (25 mL), and then cultured with shaking at 30° C. at 200 rpm for 20 hours. The seed culture medium (1 mL) was inoculated into each corner-baffled flask (250 mL) containing the L-threonine production medium (24 mL) below, and then cultured with shaking at 30° C. at 200 rpm for 48 hours.

L-Threonine Production Medium (pH 7.2)

glucose 30 g, $KH_2PO_4$ 2 g, urea 3 g, $(NH_4)_2SO_4$ 40 g, peptone 2.5 g, CSL (Sigma) 5 g (10 mL), $MgSO_4$ $7H_2O$ 0.5 g, leucine 400 mg, $CaCO_3$ 20 g (based on 1 L of distilled water)

After the culture, the amounts of various amino acids produced were measured using HPLC. The concentrations of the amino acids in the culture media for the top 5 strains, which were shown to have excellent L-threonine-producing abilities among the 126 strains experimented on, are shown in Table 1. The 5 candidate strains confirmed through the above procedure were named KFCC10881-1 to KFCC10881-5.

TABLE 1

Experiments on L-threonine production of excellent AHV-resistant strains

| | OD | Thr | Hse | Gly | Ile | Lys | Thr + Hse + Gly + Ile |
|---|---|---|---|---|---|---|---|
| KFCC10881 | 60.1 | 0.0 | 0.1 | 0.2 | 0.0 | 12.3 | 0.3 |
| KFCC10881-1 | 53.6 | 4.1 | 1.3 | 1.4 | 1.2 | 2.0 | 8.0 |
| KFCC10881-2 | 53.3 | 2.2 | 0.9 | 1.0 | 1.1 | 8.3 | 5.2 |

TABLE 1-continued

Experiments on L-threonine production of excellent AHV-resistant strains

| | OD | Thr | Hse | Gly | Ile | Lys | Thr + Hse + Gly + Ile |
|---|---|---|---|---|---|---|---|
| KFCC10881-3 | 68.5 | 1.5 | 1.2 | 1.1 | 0.2 | 10.8 | 4.0 |
| KFCC10881-4 | 59.1 | 1.2 | 0.9 | 1.0 | 0.7 | 1.9 | 3.8 |
| KFCC10881-5 | 49.6 | 2.4 | 1.1 | 1.2 | 0.9 | 5.4 | 5.6 |

As shown in Table 1, the amounts of L-threonine, L-homoserine, glycine, L-alanine, and L-isoleucine, which are produced by the 5 types of strains having resistance to AHV, were increased compared to a control group, whereas the amount of L-lysine produced was decreased.

The biosynthetic pathways of L-threonine and L-lysine are separated from aspartate-semialdehyde (hereinafter, "ASA") as a branching point. That is, the amount of L-lysine produced is decreased as the amount of L-threonine produced is increased. Accordingly, the amounts of homoserine (Hse), glycine (Gly), and L-isoleucine (Ile), which can be by-products in the L-threonine biosynthetic pathway, may be increased as the amount of L-threonine produced is increased, and thus the total amount thereof produced (Thr+Hse+Gly+Ile) was also confirmed.

Therefore, among the AHV-resistant strains above, the KFCC10881-1 strain, which showed a reduced amount of L-lysine production, a high amount of L-threonine production, and a high amount of total (Thr+Hse+Gly+Ile) production, was selected as the most excellent AHV-resistant strain.

Example 3: Analysis of Nucleotide Sequences of Strains Having Excellent Ability to Produce Threonine Derived from KFCC10881

To analyze the nucleotide sequences of the L-threonine biosynthesis enzymes of the strain selected in Example 2 above, the following experiment was conducted. Based on the gene information provided by the Kyoto Encyclopedia of Genes and Genomes (KEGG), each of the nucleotide sequence of hom (SEQ ID NO: 2, NCgl1136), which encodes homoserine dehydrogenase of *Corynebacterium glutamicum* ATCC13032, and the nucleotide sequence of thrB (SEQ ID NO: 3, Gene No. NCgl1137), which encodes homoserine kinase, were obtained. Both hom and thrB genes are known to have an operon structure (Peoples et al., *Mol. Biol.* 2(1):63-72, 1988).

To obtain the DNA fragment containing the hom-thrB operon of the selected strain PCR was carried out using the genomic DNA of the strain as a template and a primer set of SEQ ID NO: 4 and SEQ ID NO: 5. PfuUltra™ high-fidelity DNA polymerase (Stratagene) was used as a polymerase for the PCR reaction. PCR conditions were as follows: 30 cycles of denaturation at 96° C. for 30 seconds, annealing at 52° C. for 30 seconds, and polymerization at 72° C. for 3 minutes. As a result, it was possible to amplify a gene fragment (2,778 bp; SEQ ID NO: 6), which includes the nucleotide sequence (300 bp) containing a promoter region upstream of the initiation codon of SEQ ID NO: 2 to include the 200 bp downstream of the termination codon of SEQ ID NO: 3.

The nucleotide sequence was determined using the prepared primers by an ABI PRISM 3730XL Analyzer (96 capillary type; Applied Biosystems). In the nucleotide sequence corresponding to hom of the hom-thrB operon in the KFCC10881-1 strain, guanine (i.e., the nucleotide at position 1,220 of SEQ ID NO: 2) was modified to adenine, and thus the CGT gene codon encoding an arginine residue was modified to the CAT gene codon encoding a histidine residue (hereinafter, "R407H modification"; SEQ ID NO: 7). Meanwhile, no modification was discovered in the thrB gene corresponding to SEQ ID NO: 3.

From the nucleotide sequence analyses above, it was possible to conclude that the feedback inhibition by L-threonine was desensitized by the modification of arginine (i.e., the 407$^{th}$ amino acid residue) of the Hom (SEQ ID NO: 8) in the KFCC10881-1 strain to histidine (hereinafter, "R407H modification").

Example 4: Preparation of Novel Strains to which Homoserine Dehydrogenase is Introduced A primer set of SEQ ID NO: 9 and SEQ ID NO: 10 was prepared so as to prepare strains in which the variant (R407H) identified in Example 2 was introduced to their wild-type strains.

To prepare strains to which each of the R407H hom modification is introduced, PCR was carried out using the genomic DNA extracted from the KFCC10811-1 strain as a template and the primer set of SEQ ID NO: 9 and SEQ ID NO: 10. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 2 minutes. As a result, a gene fragment (1,668 bp) including a promoter region (about 300 bp) of the hom gene (1,338 bp) was obtained. The amplified product was purified using a PCR purification kit (QIAGEN) and used as an insert DNA fragment for the preparation of a vector. Meanwhile, after treating with restriction enzyme SmaI, the ratio of the molar concentration (M) of the pDZ vector (KR Patent No. 10-0924065) heat-treated at 65° C. for 20 minutes to the insert DNA fragment amplified by the PCR above was set to be 1:2, and the vector was cloned using an Infusion Cloning Kit (TaKaRa) according to the manufacturer's manual, and thereby the vector for introducing the R407H modification into the chromosome, pDZ-R407H, was prepared.

The pDZ-R407H vector was transformed into *Corynebacterium glutamicum* ATCC13032 by electroporation and subjected to secondary crossover, and thereby a strain in which a substitution of a modified nucleotide was introduced into the chromosome was obtained. Using the primer sets listed below and a Mutant Allele Specific Amplification (MASA) PCR technique (Takeda et al., Hum. Mutation, 2, 112-117 (1993)), the appropriateness of the substitution was primarily determined by selecting the strain amplified using the primer set corresponding to the modified sequence (SEQ ID NO: 11 and SEQ ID NO: 12). In addition, analysis of the hom sequence of the selected strain was conducted to secondarily confirm the appropriateness of the substitution using the primer set of SEQ ID NO: 11 and SEQ ID NO: 13 and by analyzing the modified sequence in the same manner as in Example 2. The strain substituted with the modified nucleotide was named CA09-0900.

The strain CA09-0900 was deposited at the Korean Culture Center of Microorganisms (KCCM), an International Depositary Authority under the Budapest Treaty, on Dec. 14, 2018, and was assigned Accession No. KCCM12418P.

Example 5: Measurement of Activity of Homoserine Dehydrogenase

The activity of the enzyme Hom was measured in the prepared strain. The wild-type strain ATCC13032 (the control group) and the CA09-0900 strain prepared in Example 4 were each inoculated into 25 mL of the seed medium and cultured until the strains reached the late log phase. The cells of each strain were recovered by centrifugation, washed twice with a 0.1 M potassium phosphate buffer (pH 7.6), and finally suspended in 2 mL of the same buffer containing glycerol at a concentration of 30%. Each cell suspension was physically disrupted by a conventional glass bead vortexing method for 10 minutes, and each supernatant was recovered through two centrifugations (13,000 rpm, 4° C., 30 minutes) and used as a crude extract for measuring the activity of Hom. For the measurement of the activity of Hom, a coenzyme solution (0.1 mL) was added to a reaction solution for measuring the enzyme activity (a potassium phosphate (pH 7.0) buffer, 25 mM NADPH, 5 mM aspartate semialdehyde) and reacted at 30° C. The Hom enzyme activity U was defined as the number of NADPH consumed per minute according to the presence of L-threonine (0 mM, 10 mM), and the measurement results of the enzyme activity are shown in Table 2 below.

TABLE 2

Measurement of Hom activity (U) and desensitization by L-threonine

| Strain | Enzyme Activity (U) according to Amount of L-Threonine Added (mM) | |
|---|---|---|
| | 0 mM | 10 mM |
| ATCC13032 | 0.91 | 0.02 |
| CA09-0900 | 1.37 | 1.23 |

As a result of the experiment, it was confirmed that in the Hom including the R407H modification, the inhibition of the activity was reduced under the condition where 10 mM L-threonine was contained, unlike the wild-type Hom, thus confirming the occurrence of desensitization to L-threonine.

Example 6: Preparation and Evaluation of Microorganism Strains of the Genus *Corynebacterium* Having L-Threonine-Producing Ability Strains producing L-threonine were developed from the wild-type *Corynebacterium glutamicum* ATCC13032. Specifically, to resolve the feedback inhibition by aspartate kinase (lysC) (i.e., an important enzyme which is acted upon first in the threonine biosynthesis pathway), leucine (i.e., which is an amino acid at position 377 of lysC) was substituted with lysine (SEQ ID NO: 14).

More specifically, to prepare strains in which the lysC (L377K) modification is introduced, PCR was carried out using the chromosome of ATCC13032 as a template and the primers set of SEQ ID NOS: 15 and 16 or SEQ ID NOS: 17 and 18. PfuUltra™ high-fidelity DNA polymerase (Stratagene) was used as a polymerase for the PCR reaction. PCR conditions were as follows: 28 cycles of denaturation at 95° C. for 30 seconds, annealing at 55° C. for 30 seconds, and polymerization at 72° C. for 1 minute. As a result, a DNA fragment (515 bp) in the 5' upstream region and a DNA fragment (538 bp) in the 3' downstream region, with the modification site of lysC gene as the center, were each obtained. PCR was carried out with the two amplified DNA fragments as a template and the primer set of SEQ ID NO: 15 and SEQ ID NO: 18. PCR was carried out as follows: denaturation at 95° C. for 5 minutes; 28 cycles of denaturation at 95° C. for 30 seconds, annealing at 55° C. for 30 seconds, and polymerization at 72° C. for 2 minutes; and polymerization at 72° C. for 5 minutes. As a result, the DNA fragment (1,023 bp) including the modification of lysC gene, which encodes an aspartokinase variant in which leucine at position 377 is substituted with lysine, was amplified. The amplified product was purified using a PCR purification kit (QIAGEN) and used as an insert DNA fragment for the preparation of a vector. Meanwhile, after treating with restriction enzyme SmaI, the ratio of the molar concentration (M) of the pDZ vector (KR Patent No. 10-0924065) heat-treated at 65° C. for 20 minutes to the insert DNA fragment amplified by the PCR above was set to be 1:2, and the vector was cloned using an Infusion Cloning Kit (TaKaRa) according to the manufacturer's manual, and thereby the vector for introducing the L377K modification into the chromosome, pDZ-L377K, was prepared.

The prepared pDZ-L377K vector was transformed into the ATCC13032 strain and subjected to secondary crossover, and thereby a strain in which a substitution of a modified nucleotide was introduced into the chromosome was obtained. The strain was named CJP1. The CJP1 strain was named again as CA01-2307, deposited at the Korean Culture Center of Microorganisms (KCCM), an International Depositary Authority under the Budapest Treaty, on Mar. 29, 2017, and was assigned Accession No. KCCM12000P.

To clearly confirm the changes in the L-threonine production of the above strain, the modification identified in Example 4 was introduced into a gene encoding homoserine dehydrogenase. Specifically, to introduce the R407H modification into the CJP1 strain, the pDZ-R407H vector prepared in Example 4 was transformed into the CJP1 strain by electroporation and subjected to a secondary crossover, and thereby a strain in which a modified nucleotide was introduced into the chromosome was obtained. The strain substituted with a modified nucleotide was named CJP1-R407H.

TABLE 3

Confirmation of L-threonine-producing ability of prepared strains

| Strain | Amino acid (g/L) | |
|---|---|---|
| | Thr | Lys |
| CJP1 | 0.36 | 3.62 |
| CJP1-R407H | 1.50 | 2.47 |

As a result, in the strain where the modification was introduced, the amount of L-lysine produced was decreased and the amount of L-threonine produced was increased by 1.14 g/L, compared to the CJP1 strain (the control group), thus confirming a significant improvement in the effect of desensitization.

Example 7: Preparation and Evaluation of Microorganism Strains of the Genus *Corynebacterium* Producing L-Isoleucine To prepare isoleucine-producing strains, a vector was prepared for enhancing the expression of the modified gene ilvA(V323A) (*Appl. Enviro. Microbiol., December* 1996, p. 4345-4351), which encodes known L-threonine dehydratase (the first enzyme in the isoleucine biosynthesis pathway), in the strains prepared in Example 6.

Specifically, to prepare a vector for introducing a modification, which targets the gene ilvA, a pair of primers (SEQ ID NOS: 19 and 20) for amplifying the 5' upstream region and a pair of primers (SEQ ID NOS: 21 and 22) for amplifying the 3' downstream region were devised with the modification site as the center. BamHI restriction enzyme sites were inserted at each end of the primers of SEQ ID NOS: 19 and 22, and the primers of SEQ ID NOS: 20 and 21 were designed such that a nucleotide-substituted modification can be positioned at a region where a crossover is to be induced.

PCR was carried out with the chromosome of the wild-type strain as a template using the primers of SEQ ID NOS: 19, 20, 21, and 22. PCR was carried out as follows: denaturation at 95° C. for 5 minutes; 30 cycles of denaturation at 95° C. for 30 seconds, annealing at 55° C. for 30 seconds, and polymerization at 72° C. for 30 seconds; and polymerization at 72° C. for 7 minutes. As a result, a DNA fragment (627 bp) in the 5' upstream region and a DNA fragment (608 bp) in the 3' downstream region were obtained with the modification site of the gene ilvA as the center.

PCR was carried out using the two amplified DNA fragments as a template and the primer set of SEQ ID NOS: 19 and 22. PCR was carried out as follows: denaturation at 95° C. for 5 minutes; 30 cycles of denaturation at 95° C. for 30 seconds, annealing at 55° C. for 30 seconds, and polymerization at 72° C. for 60 seconds; and polymerization at 72° C. for 7 minutes. As a result, a DNA fragment (1,217 bp) was amplified, in which the DNA fragment included a modification of the gene ilvA that encodes an IlvA variant where valine at position 323 was substituted with alanine. The vector pECCG117 (KR Patent No. 10-0057684) and the DNA fragment (1,217 bp) were treated with restriction enzyme BamHI, ligated using DNA ligase, and then cloned to obtain a plasmid. The thus-obtained plasmid was named pECCG117-ilvA(V323A).

The pECCG117-ilvA(V323A) vector was introduced to the CJP1-R407H strain prepared in Example 6 by electroporation and plated on a selective medium containing kanamycin (25 mg/L) to obtain the transformed strains. The thus-obtained transformed strains were cultured by the same flask culture method of Example 2, and the concentrations of L-isoleucine in the culture media were analyzed. The results thereof are shown in Table 4 below.

TABLE 4

Confirmation of L-isoleucine-producing ability of prepared strains

| Strain | L-Isoleucine (g/L) |
|---|---|
| CJP1/pECCG117-ilvA(V323A) | 0.7 |
| CJP1-R407H/pECCG117-ilvA(V323A) | 1.4 |

As a result, it was confirmed that in the strain including the hom(R407H) modification, the L-isoleucine-producing ability was improved by 0.7 g/L compared to the control strain.

Example 8: Preparation and Evaluation of O-Acetyl-Homoserine (OAH)-Producing Strain Substituted with Modified Hom 8-1. Preparation of ATCC13032 Strain Substituted with Modified Hom The R407H modification was introduced into the hom gene of the ATCC13032 strain in the same manner as in Example 4, and the thus-prepared strain was named ATCC13032::Hom$^{FBR}$.

8-2. Deletion of metB Gene

In this Example, the metB gene encoding cystathionine gamma-synthase in the O-acetyl-homoserine degradation pathway was obtained through PCR using the chromosomal DNA of *Corynebacterium glutamicum* ATCC13032 as a template. Based on the GenBank of the National Institutes of Health (NIH GenBank), the information of the nucleotide sequence of the metB was obtained (NCBI Registration No. Ncgl2360; SEQ ID NO: 23). In addition, based on this, the primers (SEQ ID NOS: 24 and 25) containing the N-terminus and linker sequence of the metB gene and the primers (SEQ ID NOS: 26 and 27) containing the C-terminus and linker sequence of the metB gene were synthesized. PCR was carried out using the chromosomal DNA of *Corynebacterium glutamicum* ATCC13032 as a template and the oligonucleotides of the nucleotide sequences of SEQ ID NOS: 24 and 25 and SEQ ID NOS: 26 and 27 as the primer sets. PfuUltra™ high-fidelity DNA polymerase (Stratagene) was used as a polymerase. PCR was carried out as follows: 30 cycles of denaturation at 96° C. for 30 seconds, annealing at 53° C. for 30 seconds, and polymerization at 72° C. for 1 minute; and polymerization at 72° C. for 7 minutes. As a result, an amplified gene (500 bp) containing the N-terminus and linker of the metB gene and an amplified gene (500 bp) containing the C-terminus and linker of the metB gene were obtained.

PCR was carried out using the two thus-obtained amplified genes as a template and the primer set of SEQ ID NOS: 24 and 27 under the following conditions: 30 cycles of denaturation at 96° C. for 60 seconds, annealing at 50° C. for 60 seconds, and polymerization at 72° C. for 1 minute; and polymerization at 72° C. for 7 minutes. As a result, an amplified ΔmetB gene (1,000 bp), which is a metB inactivation cassette containing the N-terminal-linker-C-terminal of the metB gene, was obtained. The metB gene obtained though the PCR was treated with restriction enzymes XbaI and SalI included at the termini, and then cloned into a pDZ vector, which was treated in advance with the restriction enzymes XbaI and SalI, via ligation. Thereafter, a recombinant pDZ-ΔmetB vector in which the metB inactivation cassette is finally cloned was prepared.

The prepared pDZ-ΔmetB vector was transformed into the *Corynebacterium glutamicum* ATCC13032 and ATCC13032::Hom$^{FBR}$ strains. After secondary crossover, the *Corynebacterium glutamicum* ATCC13032 ΔmetB and ATCC13032::Hom$^{FBR}$ ΔmetB strains, in which the metB gene is inactivated on the chromosome, were obtained. The inactivated metB gene was finally confirmed by carrying out PCR using the primer set of SEQ ID NOS: 24 and 27, followed by comparing the sequence with the ATCC13032 strain in which the metB gene is not inactivated.

8-3. Deletion of metY Gene

In this Example, the metY gene encoding O-acetylhomoserine (thiol)-lyase in the 0-acetyl-homoserine degradation pathway was obtained through PCR using the chromosomal DNA of *Corynebacterium glutamicum* ATCC13032 as a template. Based on GenBank of the National Institutes of Health (NIH GenBank), the information of the nucleotide sequence of the metY gene was obtained (NCBI Registration No. Ncgl0625; SEQ ID NO: 28). In addition, based on this, the primers (SEQ ID NOS: 29 and 30) containing the N-terminus and linker sequence of the metY gene and the primers (SEQ ID NOS: 31 and 32) containing the C-terminus and linker sequence of the metY gene were synthesized.

PCR was carried out with the chromosomal DNA of *Corynebacterium glutamicum* ATCC13032 as a template using the oligonucleotides of the nucleotide sequences of SEQ ID NOS: 29 and 30 and SEQ ID NOS: 31 and 32 as the primer sets. PfuUltra™ high-fidelity DNA polymerase (Stratagene) was used as a polymerase. PCR was carried out as follows: 30 cycles of denaturation at 96° C. for 30 seconds, annealing at 53° C. for 30 seconds, and polymerization at 72° C. for 1 minute; and polymerization at 72° C. for 7 minutes. As a result, an amplified gene (500 bp) containing the N-terminus and linker of the metY gene and an amplified gene (500 bp) containing the C-terminus and linker of the metY gene were obtained. PCR was carried out using the two thus-obtained amplified genes as a template and the primer set of SEQ ID NOS: 29 and 32 under the following conditions: 10 cycles of denaturation at 96° C. for 60 seconds, annealing at 50° C. for 60 seconds, and polymerization at 72° C. for 1 minute; and polymerization at 72° C. for 7 minutes. As a result, an amplified ΔmetY gene (1,000 bp), which is a metY inactivation cassette containing the N-terminal-linker-C-terminal of the metY gene, was obtained.

The metY gene obtained through the PCR was treated with restriction enzymes XbaI and SalI included at the termini, and then cloned into a pDZ vector, which was treated in advance with the restriction enzymes XbaI and SalI, via ligation. Thereafter, a recombinant pDZ-ΔmetY vector in which the metY inactivation cassette is finally cloned was prepared.

The prepared pDZ-ΔmetY vector was transformed into the *Corynebacterium glutamicum* ATCC13032, ATCC13032::Hom$^{FBR}$, ATCC13032 ΔmetB, and ATCC13032::Hom$^{FBR}$ ΔmetB strains. After secondary crossover, *Corynebacterium glutamicum* ATCC13032 ΔmetY, ATCC13032::Hom$^{FBR}$ ΔmetY, ATCC13032 ΔmetB ΔmetY, and ATCC13032::Hom$^{FBR}$ ΔmetB ΔmetY, in which the metY gene is inactivated on the chromosome, were obtained. The inactivated metY gene was finally confirmed by carrying out PCR using the primer set of SEQ ID NOS: 29 and 32, followed by comparing the sequence with ATCC13032 in which the metY gene is not inactivated.

8-4. Preparation and Evaluation of Strain Producing O-Acetyl-Homoserine

Comparison was made between the O-acetyl-homoserine-producing abilities of the ATCC13032, ATCC13032 ΔmetB, ATCC13032 ΔmetY, ATCC13032 ΔmetBΔmetY, ATCC13032::Hom$^{FBR}$, ATCC13032::Hom$^{FBR}$ ΔmetB, ATCC13032::Hom$^{FBR}$ ΔmetY, and ATCC13032::Hom$^{FBR}$ ΔmetBΔmetY strains prepared in Examples 8-1 to 8-3, in which the metB, metY, and metBY genes are deleted and the modified hom gene is substituted therein.

Specifically, single colonies were cultured in a solid LB medium overnight in a 32° C. incubator, and one loopful of each of the single colonies was inoculated into O-acetyl-homoserine titer media (25 mL), and then the resultants were cultured at 32° C. at 250 rpm for 42 to 64 hours. The O-acetyl-homoserine from each culture was analyzed by HPLC, and the results thereof are shown in Table 5 below.

O-Acetyl-L-Homoserine Production Medium (pH 7.2)
  glucose 30 g, $KH_2PO_4$ 2 g, urea 3 g, $(NH_4)_2SO_4$ 40 g, peptone 2.5 g, CSL (Sigma) 5 g (10 mL), $MgSO_4 \cdot 7H_2O$ 0.5 g, methionine 400 mg, leucine 400 mg, $CaCO_3$ 20 g (based on 1 L of distilled water)

TABLE 5

Evaluation of O-acetyl-homoserine production

| Strains | | O-AH production (g/L) |
|---|---|---|
| ATCC13032 | — | 0.0 |
| | metB | 0.3 |
| | metY | 0.3 |
| | metBY | 0.5 |
| ATCC13032::Hom$^{FBR}$ (R407H) | — | 0.0 |
| | metB | 1.3 |
| | metY | 1.5 |
| | metBY | 3.7 |

As a result, as shown in Table 5 above, O-acetyl-L-homoserine was not accumulated when *Corynebacterium glutamicum* ATCC13032, the control strain, was cultured; whereas 0-acetyl-L-homoserine was accumulated in an amount of 0.3 g/L, 0.3 g/L, and 0.5 g/L for each of the ATCC13032 ΔmetB, ATCC13032 ΔmetY, and ATCC13032 ΔmetB ΔmetY strains, respectively, in which the metB, metY, and metBY genes are inactivated.

Additionally, in the case of the ATCC13032::Hom$^{FBR}$ strain in which the hom gene is substituted in the form of R407H, and the ATCC13032::Hom$^{FBR}$ ΔmetB, ATCC13032::Hom$^{FBR}$ ΔmetY, and ATCC13032::Hom$^{FBR}$ ΔmetB ΔmetY strains in which the metB, metY, and metBY genes are inactivated, respectively, it was confirmed that 0-acetyl-L-homoserine was accumulated in an amount of 1.3 g/L, 1.5 g/L, and 3.7 g/L for each of these strains.

Therefore, it was confirmed from the above results that the production amount of the target amino acid, of which homoserine is a precursor, can be significantly increased using the modified hom of the present disclosure.

Example 9: Preparation and Evaluation of Strains Producing L-Methionine

Example 9-1: Preparation of Recombinant Vector for Deletion of mcbR Gene

In this Example, to prepare methionine-producing strains, a vector for inactivation of the mcbR gene (J. Biotechnol. 103:51-65, 2003), which encodes known methionine and cysteine transcription regulatory proteins in the strains prepared in Example 6, was prepared.

Specifically, a recombinant plasmid vector was prepared using the method below so as to delete the mcbR gene on the chromosome of *Corynebacterium* ATCC13032. Based on the nucleotide sequences reported in the GenBank of the National Institutes of Health (NIH GenBank), the mcbR gene and its surrounding sequence (SEQ ID NO: 33) of *Corynebacterium glutamicum* were obtained.

For the purpose of mcbR-deletion, PCR was carried out using the chromosomal DNA of *Corynebacterium glutamicum* ATCC13032 as a template and the primer sets of SEQ ID NOS: 34 and 35 and SEQ ID NOS: 36 and 37 under the following conditions: denaturation at 95° C. for 5 minutes; 30 cycles of denaturation at 95° C. for 30 seconds; annealing at 53° C. for 30 seconds, and polymerization at 72° C. for 30 seconds; and polymerization at 72° C. for 7 minutes. As a result, DNA fragments (700 bp) were obtained.

A pDZ vector, which cannot be replicated in *Corynebacterium glutamicum*, and the amplified mcbR gene fragments were treated with restriction enzyme SmaI for chromosomal insertion. Thereafter, they were ligated using DNA ligase, transformed into *E. coli* DH5a, and plated on the same solid LB medium containing kanamycin (25 mg/L). Colonies transformed with the vector, in which deleted fragments of the target genes are inserted through PCR, were selected, and a plasmid was obtained using a plasmid extraction method. The thus-obtained plasmid was named pDZ-ΔmcbR.

Example 9-2: Preparation and Evaluation of Microorganism Strains of Genus *Corynebacterium* Producing L-Methionine The pDZ-ΔmcbR vector prepared in Example 9-1 by homologous recombination on the chromosome was transformed to each of the CJP1-R407H and CJP1 strains, which had been prepared in Example 6, by electroporation (van der Rest et al., Appl. Microbiol. Biotechnol. 52:541-545, 1999). Thereafter, secondary recombination was carried out on a solid medium containing X-gal. Strains in which the mcbR gene is deleted were confirmed by a PCR method with the transformed *Corynebacterium glutamicum* strains, in which the secondary recombination had been completed, using the primer set of SEQ ID NOS: 38 and 39. These recombinant strains were named "CJP1-R407HΔmcbR" and "CJP1ΔmcbR", respectively.

To analyze the L-methionine-producing ability of the prepared CJP1-R407HΔmcbR strain, the strain was cultured together with the CJP1ΔmcbR strain in the following manner.

*Corynebacterium glutamicum* CJP1/ΔmcbR and the inventive strain (*Corynebacterium glutamicum* CJP1-R407HΔmcbR) were inoculated into a 250 mL corner-baffled flask containing the seed medium below (25 mL), and then cultured with shaking at 30° C. at 200 rpm for 20 hours. Thereafter, the seed culture medium (1 mL) was inoculated into a 250 mL corner-baffled flask containing the production medium below (24 mL), and then cultured with shaking at 30° C. at 200 rpm for 48 hours. The compositions of the seed medium and production medium are as follows.

<Seed Medium (pH 7.0)> glucose 20 g, peptone 10 g, yeast extract 5 g, urea 1.5 g, KH$_2$PO$_4$ 4 g, K$_2$HPO$_4$ 8 g, MgSO$_4$.7H$_2$O 0.5 g, biotin 100 μg, thiamine HCl 1,000 μg, calcium pantothenate 2,000 μg, nicotinamide 2,000 μg (based on 1 L of distilled water)

<Production Medium (pH 8.0)> glucose 50 g, (NH$_4$)$_2$S$_2$O$_3$ 12 g, yeast extract 5 g, KH$_2$PO$_4$ 1 g, MgSO$_4$.7H$_2$O 1.2 g, biotin 100 μg, thiamine HCl 1,000 μg, calcium pantothenate 2,000 μg, nicotinamide 3,000 μg, CaCO$_3$ 30 g (based on 1 L of distilled water)

After the cultivation using the above cultivation method, the concentration of L-methionine in each culture medium was analyzed, and the results are shown in Table 6.

TABLE 6

Evaluation of L-methionine-producing abilities of prepared strains

| Strain | L-Methionine (g/L) |
|---|---|
| CJP1ΔmcbR | 0.01 |
| CJP1-R407HΔmcbR | 0.19 |

As a result, it was confirmed that in the strain including the R407H hom modification, the L-methionine-producing ability was improved by 0.18 g/L compared to the control strain.

Based on the results above, it was confirmed that the amount of L-methionine produced can be significantly increased using the modified hom of the present disclosure.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A modified homoserine dehydrogenase comprising an amino acid sequence, wherein the amino acid sequence is substituted with histidine at a position corresponding to position 407 in the amino acid sequence of SEQ ID NO: 1.

2. A polynucleotide encoding the modified homoserine dehydrogenase of claim 1.

3. A microorganism of the genus *Corynebacterium*, comprising the modified homoserine dehydrogenase of claim 1.

4. The microorganism according to claim 3, wherein the microorganism of the genus *Corynebacterium* produces homoserine or a homoserine-derived L-amino acid.

5. The microorganism according to claim 4, wherein the homoserine-derived L-amino acid is at least one kind selected from the group consisting of L-threonine, L-isoleucine, O-acetyl homoserine, and L-methionine.

6. The microorganism according to claim 3, wherein the microorganism of the genus *Corynebacterium* is *Corynebacterium glutamicum*.

7. A method for producing homoserine or a homoserine-derived L-amino acid, comprising:
    culturing in a medium a microorganism of the genus *Corynebacterium* comprising the modified homoserine dehydrogenase of claim 1; and
    recovering homoserine or a homoserine-derived L-amino acid from the cultured microorganism or cultured medium.

8. The method according to claim 7, wherein the homoserine-derived L-amino acid is at least one kind selected from the group consisting of L-threonine, L-isoleucine, O-acetyl homoserine, and L-methionine.

9. The method according to claim 7, wherein the microorganism of the genus *Corynebacterium* is *Corynebacterium glutamicum*.

10. A modified homoserine dehydrogenase that comprises an amino acid sequence that is at least 80% identical to the amino acid sequence of SEQ ID NO: 1, and has histidine at a position corresponding to position 407 in the amino acid sequence of SEQ ID NO: 1.

11. The modified homoserine dehydrogenase of claim 10, wherein the modified homoserine dehydrogenase is at least 90% identical to the amino acid sequence of SEQ ID NO: 1.

12. The modified homoserine dehydrogenase of claim 10, wherein the modified homoserine dehydrogenase is at least 95% identical to the amino acid sequence of SEQ ID NO: 1.

13. A polynucleotide encoding the modified homoserine dehydrogenase of claim 10.

14. A microorganism of the genus *Corynebacterium*, comprising the modified homoserine dehydrogenase of claim 10.

15. The microorganism according to claim 14, wherein the microorganism of the genus *Corynebacterium* produces homoserine or a homoserine-derived L-amino acid.

16. The microorganism according to claim 15, wherein the homoserine-derived L-amino acid is at least one kind selected from the group consisting of L-threonine, L-isoleucine, O-acetyl homoserine, and L-methionine.

17. The microorganism according to claim 14, wherein the microorganism of the genus *Corynebacterium* is *Corynebacterium glutamicum*.

18. A method for producing homoserine or a homoserine-derived L-amino acid, comprising:
    culturing in a medium a microorganism of the genus *Corynebacterium* comprising the modified homoserine dehydrogenase of claim 10; and
    recovering homoserine or a homoserine-derived L-amino acid from the cultured microorganism or cultured medium.

19. The method according to claim 18, wherein the homoserine-derived L-amino acid is at least one kind selected from the group consisting of L-threonine, L-isoleucine, O-acetyl homoserine, and L-methionine.

20. The method according to claim 18, wherein the microorganism of the genus *Corynebacterium* is *Corynebacterium glutamicum*.

\* \* \* \* \*